(12) United States Patent
Onyuksel et al.

(10) Patent No.: US 6,348,214 B1
(45) Date of Patent: Feb. 19, 2002

(54) MATERIALS AND METHODS FOR MAKING IMPROVED LIPOSOME COMPOSITIONS

(75) Inventors: Hayat Onyuksel, Western Springs; Israel Rubinstein, Highland Park, both of IL (US)

(73) Assignee: The Board of Trustees of the Illinois, Urbana, IL (US)

( * ) Notice: Subject to any disclaimer, the term of this patent is extended or adjusted under 35 U.S.C. 154(b) by 0 days.

(21) Appl. No.: 09/630,699

(22) Filed: Aug. 1, 2000

Related U.S. Application Data

(62) Division of application No. 09/155,368, filed as application No. PCT/US97/05161 on Mar. 28, 1997, now Pat. No. 6,197,333.
(60) Provisional application No. 60/014,363, filed on Mar. 28, 1996.

(51) Int. Cl.$^7$ ............................................. A61K 9/127
(52) U.S. Cl. ........................ 424/450; 264/4.1; 264/4.3; 264/4.6; 514/2; 514/21
(58) Field of Search ................................ 424/450, 401, 424/1.21, 9.321, 9.51, 417, 943; 430/829; 935/54; 269/44, 4.3, 4.6; 514/2, 21

(56) References Cited

U.S. PATENT DOCUMENTS

| | | | |
|---|---|---|---|
| 4,529,561 A | 7/1985 | Hunt et al. | 264/4.3 |
| 4,920,016 A | 4/1990 | Allen et al. | 424/450 |
| 5,013,556 A | 5/1991 | Woodle et al. | 424/450 |
| 5,225,212 A | 7/1993 | Martin et al. | 424/450 |
| 5,230,882 A | 7/1993 | Unger | 424/9 |
| 5,374,548 A | 12/1994 | Caras | 424/450 |
| 5,484,894 | 1/1996 | Woiszwillo | 530/410 |
| 5,514,670 A | 5/1996 | Friedman et al. | 514/2 |
| 5,534,241 A | 7/1996 | Torchilin et al. | 424/9.321 |
| 5,542,935 A | 8/1996 | Unger et al. | 604/190 |
| 5,543,390 A | 8/1996 | Yatvin et al. | 514/2 |
| 5,545,569 A | 8/1996 | Grainger et al. | 436/518 |
| 5,552,156 A | 9/1996 | Burke | 424/450 |
| 5,567,410 A | 10/1996 | Torchilin et al. | 424/9.4 |
| 5,573,934 A | 11/1996 | Hubbell et al. | 435/177 |
| 5,578,709 A | 11/1996 | Woiszwillo | 530/410 |
| 5,580,575 A | 12/1996 | Unger et al. | 424/450 |
| 5,580,853 A | 12/1996 | Sytkowski | 514/8 |
| 5,585,112 A | 12/1996 | Unger et al. | 424/450 |
| 5,587,149 A | 12/1996 | Punto et al. | 424/59 |
| 5,589,453 A | 12/1996 | Greve et al. | 514/8 |
| 5,595,722 A | 1/1997 | Grainger et al. | 424/9.2 |
| 5,612,027 A | 3/1997 | Galin et al. | 424/78.04 |
| 5,633,226 A | 5/1997 | Owen et al. | 514/2 |
| 5,635,187 A | 6/1997 | Bathurst et al. | 424/195.1 |

FOREIGN PATENT DOCUMENTS

| | | |
|---|---|---|
| JP | 0082311 | 5/1982 |
| WO | WO 93/20802 | 10/1993 |
| WO | WO 95/27496 | 10/1995 |
| WO | WO 97/35560 | 10/1997 |
| WO | WO 97/35561 | 10/1997 |

OTHER PUBLICATIONS

Alessandrini, F. et al., "Vasoactive Intestinal Peptide Enhances Lung Preservation," *Transplantation*, 56(4):964–973 (Oct., 1993).

Alexandridis, P. et al., "Temperature Effects of Structural Properties of Pluronic P104 and F108 PEO–PPO–PEO Block Copolymer Solutions," *Langmuir*, 11:1468–1476 (1995).

(List continued on next page.)

*Primary Examiner*—Gollamudi S. Kishore
(74) *Attorney, Agent, or Firm*—Marshall, Gerstein, & Borun

(57) ABSTRACT

Provided are methods for preparing improved biologically active liposome products comprising a biologically active amphipathic compound in association with a liposome. Methods for producing the liposome products as well as methods of using the liposome products in therapeutic and diagnostic techniques are also provided.

14 Claims, 7 Drawing Sheets

OTHER PUBLICATIONS

Alkan–Onyuksel, H. et al., "A Mixed Micellar Formulation Suitable for the Parenteral Administration of Taxol," *Pharmaceutical Research*, 11(2):206–212 (1994).

Alkan–Onyuksel, H. et al., "Development of Inherently Echogenic Liposomes as an Ultrasonic Contrast Agent," *Journal of Pharmaceutical Sciences*, 85(5):486–490 (May, 1996).

Allen, T.M. et al., "Large Unilamellar Liposomes with Low Uptake into the Reticuloendothelial System," *Federation European Biochemical Societies*, 223(1):42–46 (Oct., 1987).

Allen, T.M. et al., "Liposomes containing synthetic lipid derivatives of poly(ethylene glycol) show prolonged circulation half–lives in vivo," *Biochimica et Biophysica Acta*, 1066:29–36 (1991).

Almgren, M. et al., "Self–aggregation and phase behavior of poly(ethylene oxide)–poly(propylene oxide)–poly(ehtylene oxide) block copolymers in aqueous solution," *Colloid Polym Sci.*, 273:2–15 (1995).

Artwohl, J.F. et al., "Initial Characterization of Hamsters with Spontaneous Hypertension," *FASEB J.*, 10:A628 (1996).

Avidor, R. et al., "VIP–mRNA is increased in hypertensive rats," *Brain Research*, 503:304–307 (1989).

Bangham, A.D. et al., "Diffusion of Univalent Ions across the Lamellae of Swollen Phospholipids," *J. Mol. Biol.*, 13:238–252 (1965).

Beaumier, P.L. et al., "Effect of Liposome Dose on the Elimination of Small Unilamellar Sphingomyelin/Cholesterol Vesicles from the Circulation," *Research Communications in Chemical Pathology and Pharmacology*, 39(2):277–289 (Feb., 1983).

Beaumier, P.L. et al., "Effects of Liposome Size on the Degradation of Bovine Brain Sphingomyelin/Cholesterol Liposomes in the Mouse Liver," *Biochimica et Biophysica Acta*, 731:23–30 (1983).

Bedu–Addo, F.K. et al., "Interaction of Polyethyleneglycol-Phospholipid Conjugates with Cholesterol–Phosphatidylcholine Mixtures: Sterically Stabilized Liposome Formulations," *Pharmaceutical Research*, 13(5):718–724 (1996).

Berisha, H. et al., "Vasoactive intestinal peptide prevents lung injury due to xanthine oxidase," *Am. J. Physiol.*, 259:L151–L155 (1990).

Bodanszky, M. et al., "A Preferred Conformation in the Vasoactive Intestinal Peptide (VIP). Molecular Architecture of Gastrointestinal Hormones," *Bioorganic Chemistry*, 3:133–140 (1974).

Bolin, D.R. et al., "Design and Development of a Vasoactive Intestinal Peptide Analog as a Novel Therapeutic for Bronchial Asthma," *Biopolymers,(Peptide Science)* 37:57–66 (1995).

Carey, M.C. et al., "Micelle Formation by Bile Salts," *Arch Inter. Med.*, 130:506–527 (Oct., 1972).

Chiba, K. et al., "Interaction Between Lipids and Bovine Brain Calmodulin: Lysophosphatidylcholine–Induced Conformation Change," *Life Science*, 47:953–960 (1990).

Damrongchai, N. et al., "Calcium Responsive Two–Dimensional Molecular Assembling of Lipid–Conjugated Calmodulin," *Bioconjugate Chem.*, 6:264–268 (1995).

DeGrado, W.F. et al., "Induction of Peptide Conformation at Apolar/Water Interfaces. 1. A Study with Model Peptides of Defined Hydrophobic Periodicity," *J. Am. Chem. Soc.*, 107:7684–7689 (1985).

Demos, S.M. et al., "In Vitro Targeting of Antibody–Conjugated Echogenic Liposomes for Site–Specific Ultrasonic Image Enhancement," *Journal of Pharmaceutical Sciences*, 86(2):167–171 (Feb., 1997).

Fournier, A. et al., "Synthesis, Conformational Studies and Biological Activities of VIP and Related Fragments," *Peptides* 5:169–177 (1984).

Frase, L.L. et al., "Cardiovascular Effects of Vasoactive Intestinal Peptide in Healthy Subjects," *Am. J. Cardio.*, 60:1356–1361 (1987).

Fry, D.C. et al., "Solution Structure of an Analogue of Vasoactive Intestinal Peptide As Determined by Two–Dimensional NMR and Circular Dichroism Spectroscopies and Constrained Molecular Dynamics," *Biochemistry*, 28:2399–2409 (1989).

Gabizon, A. et al., "Liposome Formulations with Prolonged Circulation Time in Blood and Enhanced Uptake by Tumors," *Proc. Natl. Acad. Sci. (USA)*, 85:6949–6953 (Sep., 1988).

Gao, X. et al., "Loop diuretics attenuate bradykinin–induced increase in clearance of macromolecules in the oral mucosa," *J. Appl. Physiol.*, 80(3):818–823 (1996).

Gao, X. et al., "Vasoactive Intestinal Peptide Encapsulated in Liposomes: Effects on Systemic Arterial Blood Pressure," *Life Sciences*, 54(15): PL247–PL252 (1994).

Gozes, I. et al., "VIP: Molecular Biology and Neurobiological Function," *Molecular Neurobiology*, 3:201–236 (1989).

Gozes, I. et al., "Stearyl–Norleucine–Vasoactive Intestinal Peptide (VIP): A Novel VIP Analog for Noninvasive Impotence Treatment," *Endorinology*, 134(5):2121–2125 (1994).

Gozes, I. et al., "Superactive Lipophilic Peptides Discriminate Multiple Vasoactive Intestinal Peptide Receptors," *J. Pharmacology Experimental Therapeutics*, 273(1):161–167 (1995).

Gregoriadias, G. et al., "Fate of Protein–Containing Liposomes Injected into Rats: An Approach to the Treatment of Storage Diseases," *Eur. J. Biochem.* 24:485–491 (1972).

Gregoriadis, G. et al., "Liposomes in Drug Delivery: Clinical, Diagnostic and Ophthalmic Potential," *Drugs*, 45(1):15–28 (1993).

Haghjoo, K. et al., "Solution Structure of Vasoactive Intestinal Polypeptide (11–28)–NH$_2$, a Fragment with Analgesic Properties," *Peptide Research*, 9(6):327–331 (1996).

Hamed, M.M. et al., "Behavior of Amphipathic Helices on Analysis via Matrix Methods, with Application to Glucagon, Secretin, and Vasoactive Intestinal Peptide," *Biopolymers*, 22:1003–1021 (1983).

Hirata, Y. et al., "Functional Receptors For Vasoactive Intestinal Peptide In Cultured Vascular Smooth Muscle Cells From Rat Aorta," *Biochemical Biophysical Research Communications*, 132(3):1079–1087 (Nov., 1985).

Hjelm, R.P. Jr. et al., "Organization of Phosphatidylcholine and Bile Salt in Rodlike Mixed Micelles," *J. Phys. Chem.*, 96(21):8653–8661 (1992).

Hökfelt, T., "Neuropeptide in Perspective: The Last Ten Years," *Neuron*, 7:867–879 (1991).

Houbre, D. et al., "The Interactions of the Brain–specific Calmodulin–binding Protein Kinase C Substrate, Neuromodulin (GAP 43), with Membrane Phospholipids," *Journal Biological Chemistry*, 266(11):7121–7131 (Apr., 1991).

Hristova, K. et al., "Effect of Bilayer Composition on the Phase Behavior of Liposomal Suspensions Containing Poly(ethylene glycol)– Lipids," *Macromolecules*, 28(23):7793–7799 (1995).

Hristova, K. et al., "Phase Behavior of a Lipid/PolymerLipid Mixture in Aqueous Medium," *Macromolecules*, 28:991–1002 (1995).

Hwang, K.J., "Liposome Pharmacokinetics," in *Liposomes from Biophysics to Therapeutics*, Ostro, M.J. (Ed.), Marcel Dekker, Inc., New York, pp. 109–156 (1987).

Kaiser, E.T. et al., "Peptides with Affinity for Membranes," *Ann. Rev. Biophys. Biophysical Chem.*, 16:561–581 (1987).

Kates, M., in *Laboratory Techniques in Biochemistry and Molecular Biology: Techniques in Lipidology Isolation, Analysis and Identification of Lipids*, Work, T.S. et al., (Eds.) North–Holland/American Elsevier, New York, New York, USA, pp. 354–356 (1972).

Kedar, E. et al., "Delivery of Cytokines by Liposomes. I. Preparation and Characterization of Interleukin–2 Encapsulated in Long–Circulating Sterically Stabilized Liposomes," *Journal of Immunotherapy*, 16:47–59 (1994).

Kenworthy, A.K. et al., "Structure and Phase Behavior of Lipid Suspensions Containing Phospholipids with Covalently Attached Poly(ethylene glycol)," *Biophysical Journal*, 68:1903–1920 (May, 1995).

Kirby, C. et al., "Dehydration–Rehydration Vesicles: A Simple Method for High Yield Drug Entrapment in Liposomes," *Biotechnology*, pp. 979–984 (Nov. 1984).

Kirby, C. et al., "Effect of the Cholesterol Content of Small Unilamellar Liposomes on their Stability in vivo and in vitro," *Biochem. J.*, 186:591–598 (1980).

Klibanov, A.L. et al., "Activity of amphipathic poly(ethylene glycol) 5000 tp prolong the circulation time of liposomes depends on the liposome size and is unfavorable for immunoliposome binding to target," *Biochimica Biophysica Acta*, 1062:142–148 (1991).

Klibanov, A.L. et al., "Amphipathic polyethyleneglycols effectively prolong the circulation time of liposomes," *FEBS Lett.*, 268(1):235–237 (Jul., 1990).

Krejs, G.J., "Effect of Vasoactive Intestinal Peptide in Man," *Am. N.Y. Acad. Sci.*, 527:501–507 (1988).

Lasic, D. et al., *Stealth Liposomes*, Lasic, D. et al., (Eds.), CRC Press, Inc., Boca Raton, FL, pp. 1–289 (1995).

Litzinger, D.C. et al., "Effect of Liposome Size on the Circulation Time and Intraorgan Distribution of Amphipathic Poly(ethylene glycol)–Containing Liposomes," *Biochimica et Biophysica Acta*, 1190:99–107 (1994).

Liu, D. et al., "Role of liposome size and RES blockade in controlling biodistribution and tumor uptake of $GM_1$–containing liposomes," *Biochimica et Biophysica Acta*, 1104:95–101 (1992).

Lutz, E.M. et al., "The $VIP_2$ receptor: molecular characterisation of a cDNA encoding a novel receptor for vasoactive intestinal peptide," *FEBS Lett*, 334(1):3–8 (Nov., 1993).

MacDonald, R.C. et al., "Small–Volume Extrusion Apparatus for Preparation of Large, Unilamellar Vesicles," *Biochimica et Biophysica Acta*, 1061:297–303 (1991).

Malhotra, R.K. et al., "Vasoactive Intestinal Polypeptide and Muscarine Mobilize Intracellular $Ca^{2+}$ through Breakdown of Phosphoinositides to Induce Catecholamine Secretion," *Journal of Biological Chemistry*, 263(5):2123–2126 (1988).

Maruyama, K. et al., "Effect of Molecular Weight in Amphipathic Polyehtyleneglycol on Prolonging the Circulation Time of Large Unilamellar Liposomes," *Chem. Pharm. Bull.*, 39(6):1620–1622 (1991).

Mayhan, W.G. et al., "Acetylcholine Induces Vasoconstriction in the Microcirculation of Cardiomyopathetic Hamsters: Reversal by L–Arginine," *Biochemical and Biophysical Research Communications*, 184(3):1372–1377 (May, 1992).

Mayhan, W.G. et al., "The Effect of Altering the External Calcium Concentration and a Calcium Channel Blocker, Verapamil, on Microvascular Leaky Sites and Dextran Clearance in the Hamster Cheek Pouch," *Microvascular Research*, 28:159–179 (1984).

Morice, A. et al., "Vasoactive Intestinal Peptide Causes Bronchodilatation and Protects Against Histamine–Induced Bronchoconstriction in Asthmatic Subjects," *Lancet*, 262(8361):1225–1227 (Nov., 1983).

Muller, J. et al., "VIP as a Cell–Growth and Differentiation Neuromodulator Role in Neurodevelopment," *Molecular Neurobiology*, 10:115–134 (1995).

Muranushi, N. et al., "Effect Of Fatty Acids And Monoglycerides On Permeability Of Lipid Bilayer," *Chemistry and Physics of Lipids*, 28:269–279 (1981).

Musso, G.F. et al., "Development of Helix–Based Vasoactive Intestinal Peptide Analogues: Identification of Residues Required for Receptor Interaction," *Biochemistry*, 27:8174–8181 (1988).

Nivaggioli, T. et al., "Fluorescence Probe Studies of Pluronic Copolymer Solutions as a Function of Temperature," *Langmuir*, 11(3):730–737 (1995).

Noda, Y. et al., "Partitioning of Vasoactive Intestinal Polypeptide into Lipid Bilayers," *Biochimica et Biophysica Acta*, 1191:324–330 (1994).

Nucci, M.L. et al., "The Therapeutic Value of Poly(ethylene glycol)–Modified Proteins," *Advanced Drug Delivery Reviews*, 6:133–151 (1991).

Ollerenshaw, S. et al., "Absence of Immunoreactive Vasoactive Intestinal Polypeptide in Tissue from the Lungs of Patients with Asthma," *New England Journal of Medicine*, 320:1244–1248 (May, 1989).

Omary, M.B. et al., "Identification of Nuclear Receptors for VIP on a Human Colonic Adenocarcinoma Cell Line," *Science*, 238:1578–1581 (1987).

Patel, M. et al., "Simplified Preparation of Vasoactive Intestinal Peptide in Sterically Stabilized Liposomes," *Proceedings of International Controlled Release Bioactive Materials*, 24:913–914 (1997).

Patel, M., "Study of Interactions Between Vasoactive Intestinal Peptide and Phospholipid Vesicles and Micelles," Masters Thesis, University of Illinois at Chicago, Chicago, Illinois (1997).

Paul, S. et al., "Regulatory Aspects of the Vasoactive Intestinal Peptide Receptor in Lung," *Ann. N.Y. Acad. Sci.*, 527:282–295 (1988).

Paul, S., "Vasoactive Intestinal Peptide: Its Interactions with Calmodulin and Catalytic Antibodies," *Neurochem. Int.*, 23(3):197–214 (1993).

Raud, J., "Intravital Microscopic Studies on Acute Mast Cell–Dependent Inflammation," *Acta Physiologica Scandinavica Supplementum 578:*1–58 (1989).

Robinson, R.M. et al., "Lipid–Induced Conformational Changes in Glucagon, Secretin, and Vasoactive Intestinal Peptide," *Biopolymers*, 21(6):1217–1228 (Jun. 1982).

Rorstad, O.P. et al., "Selectivity for Binding of Peptide Analogs to Vascular Receptors for Vasoactive Intestinal Peptide," *Molecular Pharmacology*, 37:971–977 (1990).

Rubinstein, I. et al., "Tissue Angiotensin I–Converting Enzyme Activity in Spontaneously Hypertensive Hamsters," Biochemical and Biophysical Research Communications, 183(3):1117–1123 (Mar., 1992).

Rubinstein, I. et al., "Cigarette Smoke Extract Attenuates Endothelium–Dependent Arteriolar Dilatation In Vivo," *Am. J. Physiol.*, 261 (*Heart Circ. Physiol.* 30):H1913–H1918 (1991).

Rubinstein, I., "L–Arginine Dilates Cheek Pouch Arterioles in Hamsters with Hereditary Cardiomyopathy but not in Controls," *J. Lab. Clin. Med.,* 125:313–318 (1995).

Said, S.I., "Vasoactive Intestinal Peptide (VIP) and Related Peptides as Anti–Asthma and Anti–Inflammatory Agents," *Biomedical Research,* 13(Supplement 2):257–262 (1992).

Said, S.I., "Vasoactive Intestinal Polypeptide (VIP): Current Status," *Peptides,* 5:143–150 (1984).

Said, S.I., "Vasoactive Intestinal Polypeptide: Biological Role in health and Disease," *Trends Endocrinology Metab.,* 2(3):107–112 (1991).

Saletu, B. et al., "Comparative Bioavailability Studies with a New Mixed–micelles Solution of Diazepam Utilizing Radioreceptor Assay, Psychometry and EEG Brain Mapping," *International Clinical Psychopharmacology,* 3:287–323 (1988).

Sansom, .S.P., "the Biophysics of Peptide Models of Ion Channels," *Prog. Biophys. Molec. Biol.,* 55:139–235 (1991).

Séjourné et al., "Development of a Bioactive Formulation of Vasoactive Intestinal Peptide in Sterically Stabilized Liposomes," Pharm. Res., 13(Suppl. 9):S–95 (1996).

Séjourné, F. et al., "Mechanisms of vasodilation elicited by VIP in sterically stabilized liposomes in vivo," *American Journal of Physiology,* 273:R287–R292 (1997).

Séjourné, F. et al., "Development of a Novel Bioactive Formulation of Vasoactive Intestinal Peptide in Sterically Stabilized Liposomes," *Pharmaceutical Research,* 14(3):362–365 (1997).

Shiraga, H. et al., "Inhibition of calmodulin–dependent myosin light–chain kinase by growth–hormone–releasing factor and vasoactive intestinal peptide," *Biochem. J.,* 300:901–905 (1994).

Smiley, J.D., "Southwestern Internal Medicine Conference: The Many Faces of Scleroderma," *American Journal Medical Sciences,* 304:319–333 (1992).

Soloviev, A.I., et al., "Phospholipid Vesicles (Liposomes) Restore Endothelium–Dependent Cholinergic Relaxation in Throacic Aorta from Spontaneously Hypertensive Rats," *J. Hypertension,* 11:623–627 (1993).

Sreedharan, S.P. et al., "Human Vasoactive Intestinal Peptide Receptors Expressed By Stable Transfectants Couple To Two Distinct Signaling Pathways," *Biochemical Biophysical Research Communications,* 203(1):141–148 (Aug., 1994).

Stallwood, D. et al., "Identity of a Membrane–bound Vasoactive Intestinal Peptide–binding Protein with Calmodulin," *Journal of Biological Chemistry,* 267(27):19617–19621 (Sep., 1992).

Suzuki, H. et al., "Encapsulation of VIP into Liposomes Restores Vasorelaxation in Hypertension in Situ," *American Journal of Physiology,* 271(*Heart Circ. Physiol.,* 40):H282–H287 (1996).

Suzuki, H., et al., "Encapsulation of Vasoactive Intestinal Peptide into Liposomes: Effects on Vasodilation in Vivo," *Life Sciences,* 57(15):1451–1457 (1995).

Suzuki, H. et al., "Neutral Endopeptidase Modulates VIP-Induced Vasodilation in Hamster Cheek Pouch Vessels In Situ," *Am. J. Physiol.,* 271(2 pt. 2):R393–397 (Aug., 1996).

Szucs, M., et al., "Lyophilization and Rehydration of Polymer–coated Lipid Vesicles Containing a Lipophilic Chelator in the Presence of Sucrose: Labeling with $^{99m}$Tc and Biodistribution Studies," *Nucl. Med. Biol.,* 22(2):263–268 (1995).

Theriault, Y. et al., "Structural Determination of the Vasoactive Intestinal Peptide by Two–Dimensional H–NMR Spectroscopy," *Biopolymers,* 31:459–464 (1991).

Torchilin, V.P. et al. "Polymers on the Surface of Nanocarriers: Modulation of Carrier Properties and Biodistribution," *Polymer Science,* 36(11):1585–1598 (1994).

Torchilin, V.P., "Polymer–coated long–circulating microparticulate pharmaceuticals," *J. Microencapsulation,* 15(1):1–19 (1998).

Trubetskoy, V. et al., "Micellar Solubilization of Poorly Soluble or Amphiphilic Substances Using Polyoxyethylene-Lipid Conjugates," *Proceedings of International Symposium on Controlled Release Bioactive Materials,* 22:452–453 (1995).

Trubetskoy, V.S. et al., "Stable Polymeric Micelles: Lymphangiographic Contrast Media for Gamma Scintigraphy and Magnetic Resonance Imaging," *Acad. Radiol.,* 3:232–238 (1996).

Trubetskoy, V.S. et al., "Polyethyleneglycol based micelles as carriers of therapeutic and diagnostic agents," *S.T.P. Pharma Sciences,* 6(1):79–86 (1996).

Trubetskoy,V.S. et al., "Use of polyoxyethylene–lipid conjugates as long–circulating carriers for delivery of therapeutic and diagnostic agents," *Advanced Drug Delivery Reviews,* 16:311–320 (1995).

Watala, C., et al., "Melittin–Induced Alterations in Dynamic Properties of Human Red Blood Cell Membranes," *Chem-Biol. Interactions,* 82:135–149 (1992).

Weissig, V. et al., "A Micellar Delivery System For Dequalinium," *Proceed. Int'l. Symp. Control. Rel. Bioact. Mater.,* 25:415–416 (1998).

Weissig, V. et al., "Accumulation of Protein–Loaded Long–Circulating Micelles and Liposomes in Subcutaneous Lewis Lung Carcinoma in Mice," *Pharmaceutical Research,* 15(10):1552–1556 (1998).

Weissig, V. et al., "Micellar Delivery System For Dequalinium–A Lipophilic Cationic Drug With Anticarcinoma Activity," *Journal of Liposome Research,* 8(3):391–400 (1998).

Woodle, M.C. et al., "Improved Long Circulating (Stealth®) Liposomes Using Synthetic Lipids," *Proceed. Intern. Symp. Control. Rel. Bioact. Mater.,* 17:77–78 (1990).

Woodle, M.C. et al., "Sterically stabilized liposomes," *Biochimica et Biophysica Acta,* 113:171–199 (1992).

Woodle, M.C. et al., "Versatility in Lipid Compositions Showing Prolonged Circulation with Sterically Stabilized Liposomes," *Biochimica et Biophysica Acta,* 1105:193–200 (1992).

Woodle, M.C. et al., "Prolonged Systemic Delivery of Peptide Drugs by Long–Circulating Liposomes: Illustration with Vasopressin in the Brattleboro Rat," *Pharmaceutical Research,* 9(2):260–265 (1992).

Yokoyama, M. et al., "Preparation of adriamycin–conjugated poly(ethylene glycol)–poly (aspartic acid) block copolymer," *Makromal Chem. Rapid Commun.,* 8:431–435 (1987).

Zareie, H.M. et al., "STM images of PDLLA–PEG copolymer miscelles," *Colloids and Surfaces A: Physicochemical and Engineering Aspects,* 112:19–24 (1996).

Zia, H. et al., "Breast Cancer Growth Is Inhibited by Vasoactive Intestinal Peptide (VIP) Hybrid, a Synthetic VIP Receptor Antagonist," *Cancer Research,* 56:3486–3489 (Aug., 1996).

Zorn, N.E. et al., "Vasoactive Intestinal Peptide (VIP) Activation of Nuclear Protein Kinase C in Purified Nuclei of Rat Splenocytes," *Biochemical Pharmacology,* 40:2689–2694 (1990).

MATERIALS AND METHODS FOR MAKING IMPROVED LIPOSOME COMPOSITIONS

This application is a divison of 09/155,368, filed Dec.18, 1998, now U.S. Pat. No. 6,197,333 which is a 371 of PCT/US97/05161 filed Mar. 28, 1997, which claims priority to U.S. Provisional Application No. 60/014,363, filed Mar. 28, 1996.

BACKGROUND OF THE INVENTION

The present invention relates generally to biologically active compounds and more specifically to compounds and peptides which are amphipathic, i.e., have both hydrophilic and hydrophobic portions. Specifically, the invention relates to improved methods for the delivery and presentation of amphipathic peptides in association with liposomes for both diagnostic and therapeutic uses.

Of particular interest to the present invention are the biologically active amphipathic peptides which are members of the family of peptide compounds including vasoactive intestinal peptide (VIP) and growth hormone releasing factor (GRF). More specifically, the invention relates to improved therapeutic methods for delivering peptides in the VIP/GRF family of peptides to targeted tissues through use of improved liposome compositions comprising a member of the VIP/GRF family of peptides and biologically active analogues thereof.

VIP is a 28-amino acid neuropeptide which is known to display a broad profile of biological actions and to activate multiple signal transducing pathways. See, Said. *Peptides* 5 (Suppl. 1):149–150 (1984) and Paul and Ebadi, *Neurochem. Int.* 23:197–214 (1993). A Schiff-Edmundson projection of VIP as a $\pi$-helix reveals segregation of apolar and polar residues onto the opposite faces of the helix and that this amphipathic character is also evident when VIP is modeled as a distorted $\alpha$-helix, which is reported in Musso, et al., *Biochemistry* 27:8147–8181 (1988). A correlation between the helixforming tendency of VIP analogues and their biological activity is described in Bodan et al., *Bioorgan. Chem.* 3:133–140 (1974). In pure water, the spectral characteristics of VIP are consistent with those of a random coil. However, organic solvents and anionic lipids induce helical-information in the molecule. See, Robinson et al., *Biopolymers* 21:1217–1228 (1983); Hamed, et al., *Biopolymers* 22 :1003–1021 (1983); and Bodanszky, et al,*Bioorganic Chem.* 3:133–140 (1974).

Short peptides capable of forming amphipathic helices are known to bind and penetrate lipid bilayers. See, Kaiser and Kezdy, *Ann. Rev. Biophys. Biophysical Chem.* 15:561–581 (1987) and Sansom, *Prog. Biophys. Molec. Biol.* 55:139–235 (1991). Examples include model peptides like (LKKLLKL-), which are disclosed in DeGrado and Lear,*J. Am. Chem. Soc.* 107:7684–7689 (1985), and the 26-residue bee venom peptide, melittin, disclosed in Watata and Gwozdzinski, *Chem-Biol. Interactions* 82:135–149 (1992). Possible mechanisms for the binding include alignment of peptide monomers parallel to the surface of the bilayer mediated by electrostatic interactions between polar amino acids and phospholipid head groups, and insertion of peptide aggregates into the apolar bilayer core, stabilized in part, by the hydrophobic effect. See. Sansom, *Prog. Biophys. Molec. Biol.* 55:139–235 (1991).

VIP belongs to a family of homologous peptides, other members of which include peptide histidine isoleucine (PHI), peptide histidine methionine (PHM), growth hormone releasing factor (GRF), pituitary adenylate cyclase activating peptide (PACAP), secretin and glucagon. Like VIP, the other members of the VIP/GRF family of peptides, and biologically active analogues thereof, can form amphipathic helices capable of binding lipid bilayers. The biological action of members of the VIP/GRF family of peptides are believed to be mediated by protein receptors expressed on the cell surface and intracellular receptors and it has recently been demonstrated that calmodulin is likely to be the intracellular receptor for VIP [Stallwood, et al.,*J. Bio. Chem.* 267:19617–19621 (1992); and Stallwood, et al., *FASEB J.* 7:1054 (1993)].

A major factor limiting in vivo administration of VIP has been its reduced bioavailability at target tissues mostly because of proteolytic degradation, hydrolysis, and/or a multiplicity of conformations adopted by the peptide. It has been speculated that intracellular delivery of VIP alone and/or VIP-calmodulin mixtures could bypass the requirement for cell-surface binding of the peptide and thus enhance the biological actions of the peptide. Provision of the peptides expressed in and on liposomes would possibly permit intracellular delivery, since lipid bilayers of liposomes are known to fuse with the plasma membrane of cells and deliver entrapped contents into the intracellular compartment.

Characterization of the structure and properties of liposomes led to many proposed uses for the vesicle as vehicles to effect targeted drug delivery, most of which failed to materialize for any of a number of various reasons. Most prominently, the therapeutic parenteral use of conventional liposomes was found to be limited because of rapid uptake into the reticuloendothelial system by mononuclear phagocytic cells [Gregoriadias and Ryman, *Eur. J. Biochem.* 27:485–491 (1972); Beaumier, and Hwang, *Biochem. Biophys. Acta* 731:23–30 (1983)]. Uptake by this particular cell type is advantageous under the limited conditions wherein the targeted cell or tissue itself is part of the reticuloendothelial system, but uptake by phagocytic cells generally leads to degradation of compounds to be delivered, thereby posing a serious drawback to delivering a compound to other cell or tissue types.

In attempts to overcome problems inherent to liposome drug delivery, research turned to several approaches including identification of compounds which would be released back into the blood following liposome uptake by the-reticuloendothelial system, alternatives to intravenous liposome administration, and use of various compounds, for example, cholesterol, to increase liposome stability in the bloodstream [Kirby, et al., *Biochem. J.* 186:591–598 (1980); Hwang, in *Liposomes from biophysics to therapeutics*, Ostro (ed.) Marcel Decker: New York (1987) pp. 109–156; Beaumier, et al., *Res. Comm. Chem. Pathol. Pharmacol.* 39:227–232 (1983)]. Still other investigations examined various lipid compositions to form the liposome bilayer which more closely mimic the naturally occurring bilayer of red blood cell. Such efforts led to increased liposome half-life in circulation [Allen and Chonn, *FEBS Lett.* 223:42–46 (1987); Gabizon and Papahadjopoulos, *Proc. Natl. Acad. Sci. (USA)* 85:6949–6953 (1988)].

PCT Publication WO 95/27496 and Gao, et al., *Life Science* 54:247–252 (1994) describe the use of liposomes for delivery of VIP in comparison to its delivery in aqueous solution. Encapsulation of VIP in liposomes was found to protect the peptide from proteolytic degradation and to significantly enhance the ability of VIP and to effect a decrease in mean arterial pressure in comparison to VIP in aqueous solution in hypertensive hamsters. Liposome-associated VIP was found to significantly decrease mean arterial blood pressure for a period of approximately 12 minutes, with lowest blood pressure observed almost 5 minutes after initial administration. The publication also demonstrated binding of VIP in aqueous solution to liposomes and penetration of the peptide into the liposome bilayer. It was speculated that binding of VIP to liposomes might prevent loss of peptide activity either by partitioning of the peptide into the liposome membrane, stabilizing the peptide against proteolysis, or restricting the peptide in a biologically active conformation. Whatever the reason, encapsulation of VIP in liposomes enhanced in vivo biological activity of the peptide by both prolonging the effect and increasing the magnitude of the effect in lowering blood pressure of hypertensive hamsters. Nevertheless, there remains a desire in the art to provide further improvements in the therapeutic and diagnostic delivery of biologically active peptides such as VIP.

Of interest to the present invention is the observation of increased half-life of circulating protein through conjugation of the protein to a water soluble polymer [Nucci, et al., *Adv. Drug Del. Rev.* 6:133–151 (1991); Woodle, et al., *Proc. Inten. Symp. Control. Rel. Bioacr. Mater.* 17:77–78 (1990)]. This observation led to the development of sterically stabilized liposomes (SSL) (also known as "PEG-liposomes") as an improved drug delivery system which has significantly minimized the occurrence of rapid clearance of liposomes from circulation. [lasic and Martin, *Stealth Liposomes*, CRC Press, Inc., Boca Raton, Fla. (1995)]. SSL are polymer-coated liposomes, wherein the polymer, preferably polyethylene glycol (PEG), is covalently conjugated to one of the phospholipids and provides a hydrophilic cloud outside the vesicle bilayer. This steric barrier delays the recognition by opsonins, allowing SSL to remain in circulation much longer than conventional liposomes [Lasic and Martin, *Stealth Liposomes*, CRC Press, Inc., Boca Raton, Fla. (1995); Woodle, et al, *Biochem. Biophys. Acta* 1105:193–200 (1992); Litzinger, et al., *Biochem. Biophys. Acta* 1190:99–107 (1994); Bedu Addo, et al., *Pharm. Res.* 13:718–724 (1996)]and increases the pharmacological efficacy of encapsulated agents, as demonstrated for some chemotherapeutic and anti-infectious drugs [Lasic and Martin, *Stealth Liposomes*, CRC Press, Inc. Boca Raton, Fla. (1995)]. Studies in this area have demonstrated that different factors affect circulation half-life of SSL, and ideally, the mean vesicle diameter should be under 200 nm, with PEG at a molecular weight of approximately 2,000 Da at a concentration of 5% (9–12) [Lasic and Martin, *Stealth Liposomes*, CRC Press, Inc., Boca Raton, Fla. (1995); Woodle, et al., *Biochem. Biophys. Acta* 1105:193–200 (1992); Litzinger, et al, *Biochem. Biophys. Acta* 1190:99–107 (1994); Bedu Addo, et al., *Pharm. Res.* 13:718–724 (1996)]. Preparation of SSL having these physical properties and including a bioactive compound, however, is not without complications as activity of the associated compound can be lost in preparation of SSL having desirably characteristics. This is particularly the case where an extrusion process is used to obtain small size liposomes with a narrow particle size distribution. For reasons which are not completely understood, such extrusion methods substantially reduce the biological activity peptide components associated with the liposomes. Accordingly, there remains a desire for improved liposome compositions which are sterically stable but which maintain the biological activity of associated peptide agents.

Also of interest to the present invention is the disclosure of PCT Publication WO 93/20802 which relates to multilamellar liposomes useful for enhancement of organ imaging with acoustics (ultrasound). The publication describes various liposome compositions ranging in size from 0.8 to 10 microns including a tissue specific ligand, such as an antibody, antibody fragment or a drug incorporated into the lipid bilayer, in order to facilitate tissue specific targeting. The oligolamellar liposomes are prepared by processes such as lyophilization, repeated freeze-thaw, or modified double emulsion techniques to produce internally separated bilayers. Preferred liposomes are said to range from 1.0 to 3.0 microns in diameter. It has thus far been more difficult to produce liposomes which are readily detectable by conventional ultrasound techniques less than about 0.5 microns in size. Accordingly, there remains a desire for improved liposome compositions which may be efficiently produced and which have average particle sizes less than about 0.5 microns. Moreover, there remains a desire for improved liposome compositions which are efficiently produced, stable in vivo, and provide a higher degree of resolution upon acoustic imaging.

Thus, there exists a need in the art to provide further improvements in the use of liposome technology for the therapeutic and diagnostic administration of bioactive molecules. More specifically, there remains a desire in the art for improved methods for administration of amphipathic peptides including, but not limited to, members of the VIP/GRF family of peptides in liposomes in order to achieve a more prolonged and effective therapeutic effect.

SUMMARY OF THE INVENTION

The present invention provides improved methods of preparing biologically active liposome products comprising biologically active amphipathic compounds in association with a liposome. The liposomal formulations of the invention deliver and enhance bioactivity of the biologically active peptides in a manner which provides improvements in the efficacy and duration of the biological effects of the associated peptides. Increased efficacy and duration of the biological effect is believed to result, at least in part, from interaction of the compound with the liposome in such a manner that the compound attains, and is maintained in, an active or more active conformation than the compound in an aqueous environment. The invention thus overcomes the problems associated with previous liposomal formulations, such as, but not limited to, uptake by the reticuloendothelial system, degradation of the compound, or delivery of the compound in an inactive conformation.

According to one aspect of the invention, a method is provided for preparing a biologically active liposome product comprising a biologically active amphipathic compound in association with a liposome; said method comprising the steps of a) mixing a combination of lipids wherein said combination includes at least one lipid component covalently bonded to a water-soluble polymer; b) forming sterically stabilized liposomes from said combination of lipids; c) obtaining liposomes having an average diameter of less than about 300 nm; and d) incubating liposomes from step c) with a biologically active amphipathic compound under conditions in which said compound becomes associated with said liposomes from step c) in an active conformation. According to one aspect of the invention, the biologically active liposome products comprise unilamellar liposomes which are generally preferred for therapeutic uses. According to an alternative aspect of the invention, the biologically active liposome products comprise multivesicular liposomes and are produced according to a method comprising an additional step of forming multivesicular liposomes, preferably by carrying out the steps of sequentially dehydrating and rehydrating liposomes obtained in step c) with said biologically active compound. Despite any accepted meanings to the contrary, multivesicular, multilamellar, and oligolameilar liposomes are intended as liposomes containing multiple and irregular internal "compartments", not in an "onion-like" configuration, but as set forth in FIG. 1. The multivesicular liposomes may be used in the therapeutic uses of the invention but are particularly useful in echogenic diagnostic methods of the invention in which they exhibit surprising echogenic properties.

As one aspect of the invention, the liposomes are sterically stabilized liposomes (SSL) which are produced from a combination of lipids which includes at least one lipid component covalently bonded to a water-soluble polymer. This water-soluble polymer, which is preferably polyethylene glycol (PEG), acts to sterically stabilize the resulting liposome against uptake by components of the reticuloendothelial system.

The methods of the invention are useful with any biologically active amphipathic compound which can thereby be stably maintained in an active conformation in association with or within the lipid bilayer of the liposome. Preferred amphipathic compounds include those characterized by having one or more $\alpha$- or $\pi$-helical domains in their biologically active conformation and particularly those in which polar and apolar residues are separated on opposite sides of the helix. Particularly preferred amphipathic compounds useful with the invention include any member of the vasoactive intestinal peptide (VIP)/growth hormone releasing factor (GRF) family of peptides which includes biologically active analogs thereof. The mammalian and non-mammalian VIP/GRF family of peptides includes functional analogs of VIP and GRF, peptide histidine isoleucine (PHI), peptide histidine methionine (PHM), growth hormone releasing factor (GRF), pituitary adenylate cyclase activating peptide (PACAP), secretin, and glucagon. Like VIP, other members of the VIP/GRF family of peptides, and biologically active analogues thereof, can form amphipathic helices wherein hydrophobic and hydrophilic domains of the peptide are segregated and the hydrophobic domain(s) is capable of binding lipid bilayers. The invention also contemplates receptor antagonists having enhanced bioactivity in association with liposomes prepared by a method of the invention. A particularly preferred peptide for use according to the invention is VIP. The biologically active peptide products of the invention may be utilized in a wide variety of therapeutic and diagnostic uses wherein it is desired to deliver a high level of biologically active compound or to detect targeted delivery of the liposome product as will be described below.

The invention further provides improved acoustic diagnostic products which have surprising acoustic reflectivity properties despite the fact that they are less than 1000 nm and even 300 nm in average diameter. The results using the liposomes less than 300 nm in diameter are particularly surprising in light of the teachings of the art that such liposomes should range from 0.8 to 3.0 microns in diameter. Specifically, the invention provides methods for the preparation and use of multilamellar diagnostic liposomes having an average diameter of less than about 1000 nm and particularly less than about 500 nm for improved imaging using acoustic reflectivity techniques. Herein, acoustic reflectivity, echo-reflectivity, and ultrasonic imaging are used with essentially the same meaning. The method of the invention comprises the steps of mixing a combination of lipids wherein at least one lipid component is conjugated to a water soluble polymer, forming and obtaining liposomes from the mixed combination of lipids, incubating the liposomes with a biologically active amphipathic compound, and forming multilamellar liposomes having an average diameter of about less than 1000 nm. According to a preferred embodiment of the invention, the multilamellar liposomes are formed by carrying out a lyophilization method. In a preferred embodiment, the liposomes first formed from the mixture of lipids have an average diameter of about less than 300 nm and in another embodiment these liposomes are obtained by extrusion. A preferred multilamellar liposome of the invention has an average diameter of about less than 800 nm, but most preferably has an average diameter of less than about 300 nm. In a preferred embodiment, the water soluble polymer is PEG. Biologically active compounds of the invention include those which are capable of forming $\alpha$- or $\pi$-helical domains and preferably are chosen from members of the VIP/GRF family of peptides. The most preferred biologically active compound of the invention is VIP. While not intending to be bound by any theory of their invention, it is believed that the incorporation of a water-soluble polymer such as PEG into the multivesicular liposomes may make them more capable of reflecting acoustic energy in spite of their relatively small size. While it is not completely understood why this might be the case, one possibility is that the presence of the water-soluble polymer acts to separate the walls of the multiple liposome vesicles making up a single multivesicular liposome and thus rendering that liposome better capable of reflecting acoustic radiation.

The invention further provides improved acoustic diagnostic methods wherein the small diagnostic liposomes of the invention comprising a biologically active amphipathic compound are administered in a diagnostically effective amount to a target tissue and the liposomes are detected in vivo using acoustic reflectivity. The preferred target tissue of the invention is a tumor. In one embodiment, the biologically active compound is characterized by having at least one or more $\alpha$- or $\pi$-helical domains. In a preferred embodiment, the compound is any member of the VIP/GRF family of peptides, and in a most preferred embodiment, the compound is VIP.

DETAILED DESCRIPTION OF THE INVENTION

Figure 1:
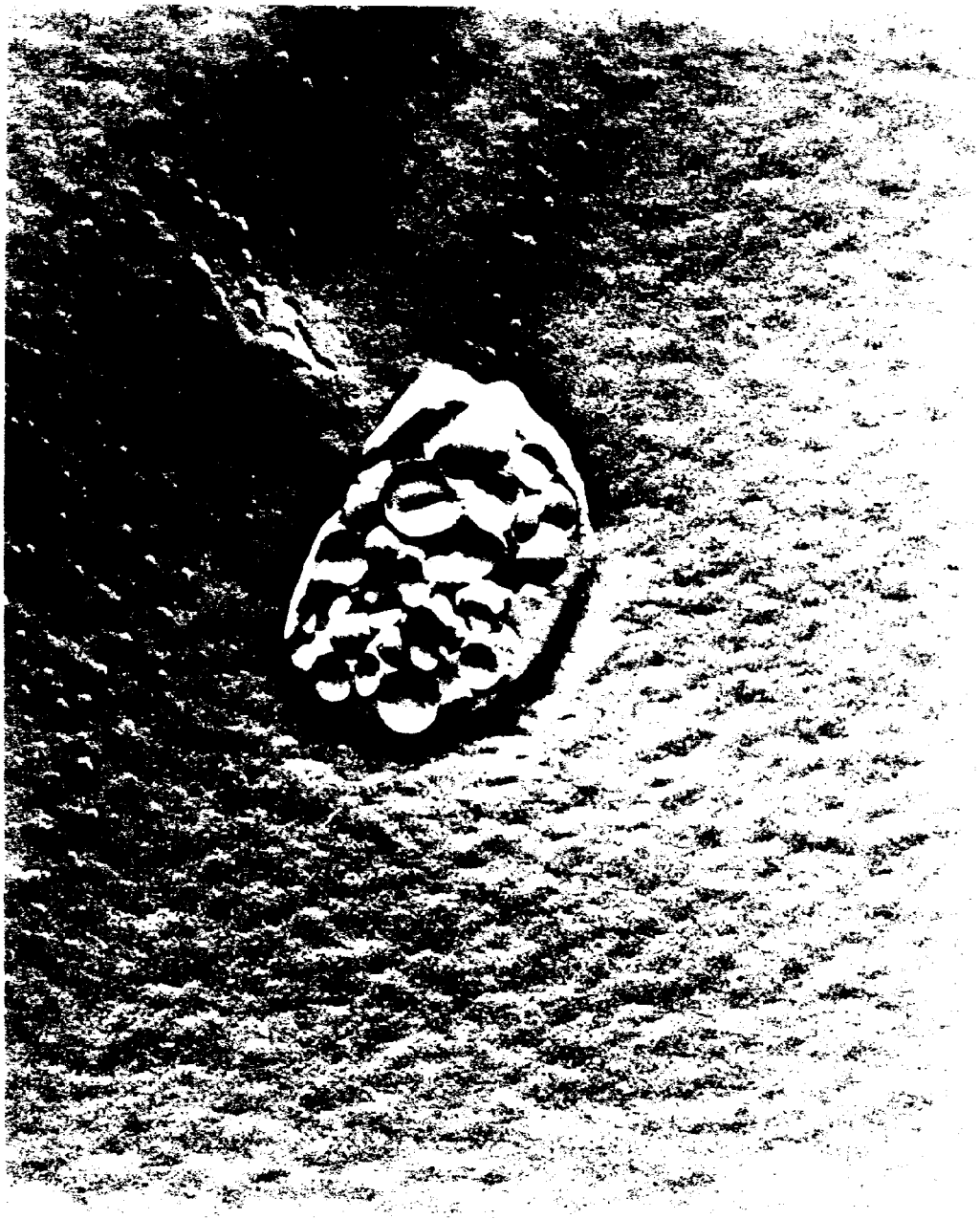
FIG. 1 is a micrograph of a multilamellar liposome of the invention.

The present invention provides improved methods of preparing biologically active liposome products comprising biologically active amphipathic compounds in association with a liposome. The preferred amphipathic compounds are characterized by having hydrophilic and hydrophobic domains segregated to the extent that the hydrophobic domain is capable of associating with or within the liposome bilayer. Compounds of the invention preferably attain a biologically active conformation in association with or within the liposome bilayer. Active conformations are those in which the desired compound is most likely to be capable of effecting its normal biological activity, for example, through receptor or ligand recognition and binding. Compounds of the invention may be characterized by having one or more discrete α- or π-helical domains which segregate the hydrophobic and hydrophilic domains. Preferred compounds of the invention are members of the VIP/GRF peptide family. The most preferred compound of the invention is VIP. While biologically active compounds are associated with the liposome bilayer, the association is not irreversible and the compound may be released either quickly or over time from association with the liposome, depending on properties of the liposome and the compound.

In contrast to prior art methods which frequently include the step of extruding peptide-containing liposomes through membranes and filters to obtain liposomes of a desired size, the liposomes according to the present invention are obtained having a diameter of less than 300 nm prior to being contacted with the active compound ingredient. Liposomes of this size may be obtained using an extrusion step which modifies liposomes, thereby reducing the size of the liposomes to a preferred average diameter prior to being incubated with the biologically active compound. Alternatively, liposomes of the desired size may be selected using techniques such as filtration or other size selection techniques. While the size-selected liposomes of the invention should have an average diameter of less than about 300 nm, it is preferred that they are selected to have an average diameter of less than about 200 nm with an average diameter of less than about 100 nm being particularly preferred. When the biologically active liposome product is a unilamellar liposome, it preferably is selected to have an average diameter of less than about 200 nm. The most preferred unilamellar liposomes of the invention have an average diameter of less than about 100 nm. It is understood, however, that multivesicular liposomes of the invention derived from smaller unilamellar liposomes will generally be larger and may have an average diameter of about less than 1000 nm. Preferred multivesicular liposomes of the invention have an average diameter of less than about 800 nm, and less than about 500 nm while most preferred multivesicular liposomes of the invention have an average diameter of less than about 300 nm.

Liposomes according to the invention may be produced from combinations of lipid materials well known and routinely utilized in the art to produce liposomes and including at least one lipid component covalently bonded to a water-soluble polymer. Lipids may include relatively rigid varieties, such as sphingomyelin, or fluid types, such as phospholipids having unsaturated acyl chains. Polymers of the invention may include any compounds known and routinely utilized in the art of SSL technology and technologies which are useful for increasing circulatory half-life for proteins, including for example polyvinyl alcohol, polylactic acid, polyglycolic acid, polyvinylpyrrolidone, polyacrylamide, polyglycerol, polyaxozlines, or synthetic lipids with polymeric headgroups. The most preferred polymer of the invention is PEG at a molecular weight between 1000 and 5000. Preferred lipids for producing liposomes according to the invention include distearoyl-phosphatidylethanolamine covalently bonded to PEG (PEG-DSPE), phosphatidylcholine (PC), and phosphatidylglycerol (PG) in further combination with cholesterol (Chol). According to a preferred embodiment of the invention, a combination of lipids and cholesterol for producing the liposomes of the invention comprise a PEG-DSPE:PC:PG:Chol molar ratio of 0.5:5:1:3.5.

The liposomes produced according to the methods of the invention are characterized by improved stability and biological activity and are useful in a variety of therapeutic diagnostic and/or cosmetic applications. According to one embodiment, the invention comprehends a composition comprising a biologically active liposome product wherein said biologically active amphipathic compound has anti-oxidant activity, anti-aging, anti-wrinkle formation or wound healing capacity. Compositions of this type may be of cosmetic or therapeutic nature. The preferred cosmetic composition includes biologically active VIP. The invention also provides an oral controlled release preparation for the treatment of a gastrointestinal disorder wherein said preparative method further comprises the step of encapsulating the biologically active liposome product in an enteric coating. The oral controlled release preparation is useful in a variety of gastrointestinal disorders including those selected from the group consisting of inflammatory bowel disorder, chronic constipation, Hirschprung's disease, achalasia, infantile hypertrophic pyloric stenosis, and ulcers. The preferred oral preparation includes biologically active VIP. Liposome preparations comprising biologically active VIP are also a promising therapeutic agent for conditions such as asthma, systemic and pulmonary hypertension, scleroderma, myocardial ischemia, impotence and baldness. The invention further provides methods for preserving a bodily organ, tissue, or cell type for storage and transplantation in a recipient comprising the step of incubating said organ in a liposome composition comprising VIP.

The invention further provides methods of administering a biologically active amphipathic compound to a target tissue comprising the steps of: preparing a biologically active liposome product comprising a biologically active amphipathic compound in association with a liposome according to the methods of the invention and administering a therapeutically effective amount of the liposome product to said target tissue. The liposome products of the invention may be administered intravenously, intraarterially, intranasally such as by aerosol administration, nebulization, inhalation, or insufflation, intratracheally, intra-articularly, orally, transdermally, subcutaneously, topically onto mucous membranes, such as, but not limited to, oral mucosa, lower gastrointestinal mucosa and conjunctiva, and directly onto target tissues.

Biologically active compounds in therapeutic methods can be administered at significantly reduced dosage levels as compared to administration of the compound alone, particularly wherein the compound has a particularly short half life or lowered bioactivity in circulation. For example, VIP in association with SSL can be expected to exhibit enhanced and prolonged bioactivity in comparison to VIP administered alone. Generally, the biologically effective amount of VIP in SSL is about 50 to 75 percent less by weight than the biologically effective amount of VIP in aqueous solution. Regardless of which bioactive compound is associated with SSL, the liposome product must be tested in order to determine a biologically effective amount required to achieve the same result effected by the compound administered by conventionally means. The worker of ordinary skill in the art would realize that the biologically effective amount of a particular compound when delivered by conventional means would serve as a starting point in the determination of an effective amount of the compound in SSL. It would therefore be highly predictive that the same and lesser dosages in SSL would be effective as well and merely routine to determine the minimum dosage required to achieve a desired biological effect. In the case of VIP administration, for example, if conventional administration would require a dosage of 20 mg, VIP in SSL would likely require 5 to 10 mg in order to achieve the same effect. Typically, a biologically effective amount of intravenously administered VIP would total 0.01 to 50 mg daily or 0.1 to 500 mg VIP in capsule form.

Association of a biologically active compound with SSL of the invention would be expected to increase the magnitude of the biological effects of the compound from about 50 to 100% over the effects observed following administration of the compound alone. Likewise, association with SSL of the invention would be expected to invoke a longer lasting biological effect.

The invention further provides improved diagnostic compositions comprising multivesicular biologically active liposome products and methods for their use comprising the steps of: preparing a biologically active liposome product comprising a biologically active amphipathic compound in association with a multilamellar liposome prepared according to the methods of the invention; administering a diagnostically effective amount of the liposome product to a target tissue; and detecting uptake or interaction of the liposome product at the target tissue. According to one aspect of the invention, the target tissue is a tumor. In one aspect of the method, the liposome product is detectably labeled with a label selected from the group including a radioactive label, a fluorescent label, a non-fluorescent label, a dye, or a compound which enhances magnetic resonance imaging (MRI). According to the preferred embodiment of the invention, the liposome product is detected by acoustic reflectivity. Diagnostic liposome products for detection by acoustic imaging generally have an average diameter of less than about 1000 nm, but preferably, the diagnostic liposome products have an average diameter of less than 600 nm and most preferably have an average diameter of less than about 300 mn.

The invention also provides use of a biologically active liposome product comprising a biologically active amphipathic compound and produced according to methods of the invention for the treatment of inflammation hypertension, allergy, Alzheimer's disease, atherosclerosis, inflammatory bowel disorder, chronic constipation, Hirschprung's disease, achalasia, infantile hypertrophic pyloric stenosis, ulcers, to enhance or decrease cell proliferation, prevent apoptosis, to promote wound healing in a body organ or tissue, and to prevent organ and tissue rejection.

Provisional application 60/014,363 the disclosure of which is hereby incorporated described results described results of use of VIP associated liposomes according to the invention. Specifically, VIP-PEG-liposomes were prepared as follows. DSPE linked to PEG (molecular weight 1,900), PG, PC, and cholesterol (molar ration 0.5:1:5:3.5) were dissolved in chloroform in a round bottom flask. The solution was dried overnight in a rotoevaporator and the resulting film desiccated overnight. The lipid film was rehydrated with saline, pH 6–7, while vortexing, and then sonicated for at least 5 minutes. The liposome preparation thus formed was extruded through stacked Nucleopore filters with pore sizes 200 nm, 100 nm, and 50 nm, respectively, until the mean size of PEG-liposome was 80–100 nm as determined by quasi elastic light scattering. VIP and trehalose, a cryoprotectant, were added to the extruded liposome preparation in polypropylene tubes, the mixture snap-freezed in ethanol- or acetone-dry ice bath for at least 20 minutes, and lyophilized overnight under similar conditions. Free VIP was separated from VIP-PEG-liposomes using Bio Gel A-5m column chromatography. The size of the PEG-liposomes in original solution and VIP-PEG-liposomes was determined by quasi elastic light scattering. Lipid concentration in PEG-liposomes in the original solution and in VIP-PEG-liposomes was determined by inorganic phosphate assay. VIP concentration in VIP-PEG-liposomes was determined by an ELISA assay.

To determine VIP concentration in VIP-PEG-liposomes, 1% sodium dodecyl sulfate, a detergent, was added to an aliquot of the VIP-PEG-liposome preparation to release associated VIP before assay. PEG-liposome and 1% sodium dodecyl sulfate alone did not interfere with the ELISA assay. Non-limiting examples from preliminary experiments using these preparations indicated increased and prolonged biological potency to target tissues of mammals as described below.

Figure 2A:
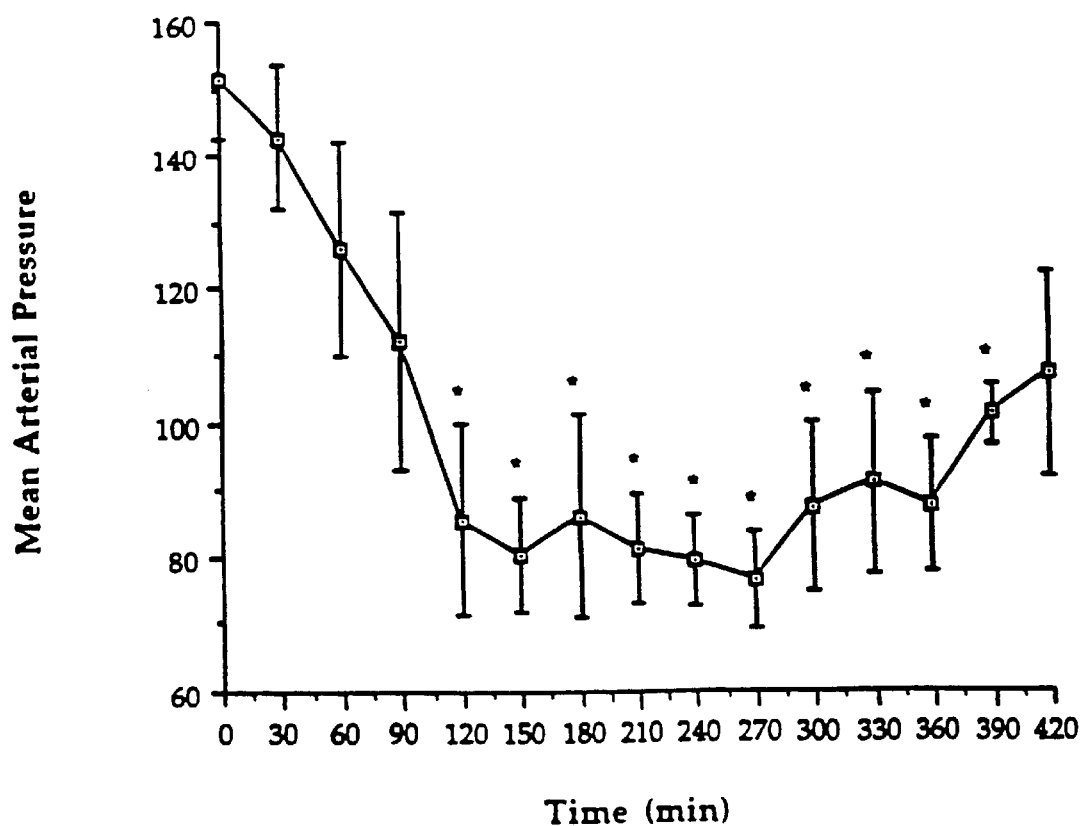
FIG. 2 shows sustained decrease in mean arterial pressure in hypertensive hamsters following treatment with a bolus injection of 1.0 nmol VIP in SSL.
Figure 2B:
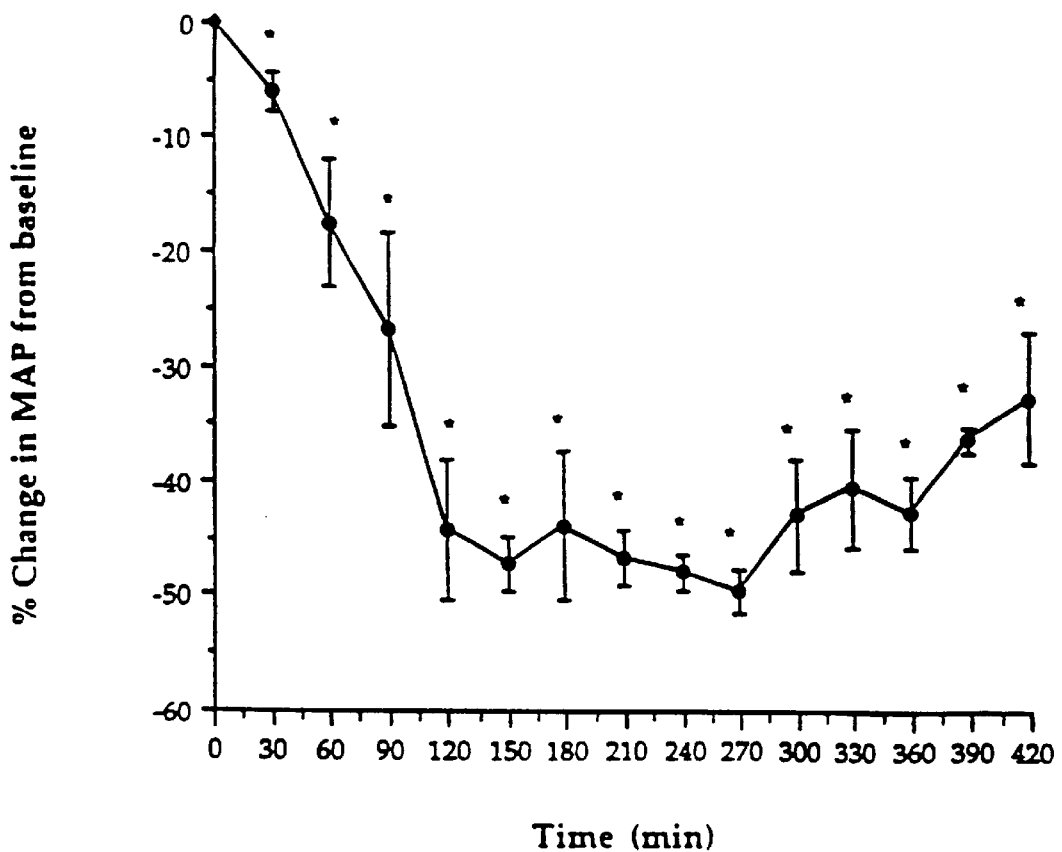

The provisional application further disclosed that a bolus intravenous injection of 1.0 nmol VIP-PEG-liposome compound acted to decrease mean arterial pressure (MAP) in hamsters with spontaneous hypertension. The results are reproduced herein as FIGS. 2A and 2B; FIG. 2A showing the actual decrease on arterial pressure and FIG. 2B showing the percent change. Data are mean values ± one standard error of the mean; an asterisk indicates statistically significant values compared to control with p value less than 0.05. Results indicated a significant, gradual and sustained decrease in mean arterial pressure reaching a nadir within 2 hours after injection of VIP-PEG-liposomes which lasted throughout the observation period of 7 hours.

Figure 3:
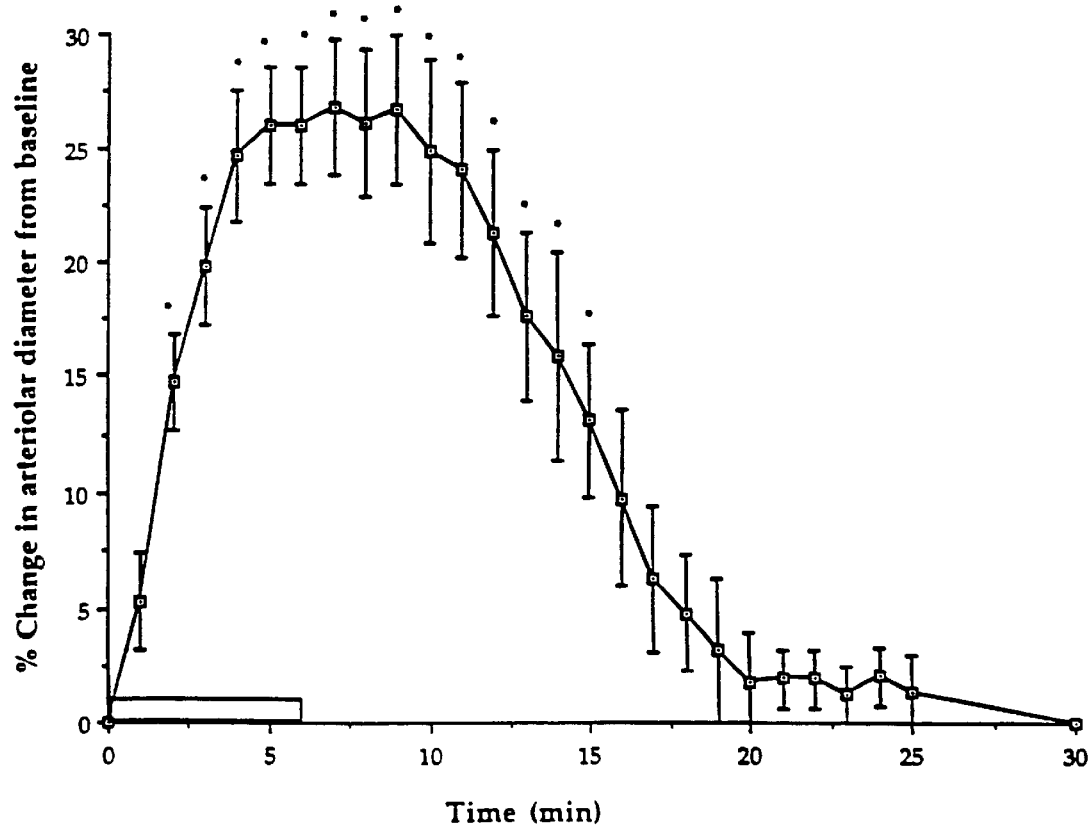
FIG. 3 shows the effects on arteriolar diameter of a 7 minute suffusion of 0.1 nmol VIP in SSL in normotensive hamsters.

According to another experiment, normotensive hamsters were suffused onto the cheek pouch for 7 minutes with 0.1 nmol VIP-PEG-liposome composition which produced a significant increase in mean arterial diameter in situ. The results of this experiment are shown in FIG. 3 with data and significance indicated for results in FIGS. 2A and 2B above. A significant increase in arteriolar diameter from baseline was observed with maximal effect within 5 minutes from the start of suffusion. Arterial diameter returned to baseline 9 minutes after suffusion was discontinued.

Figure 4:
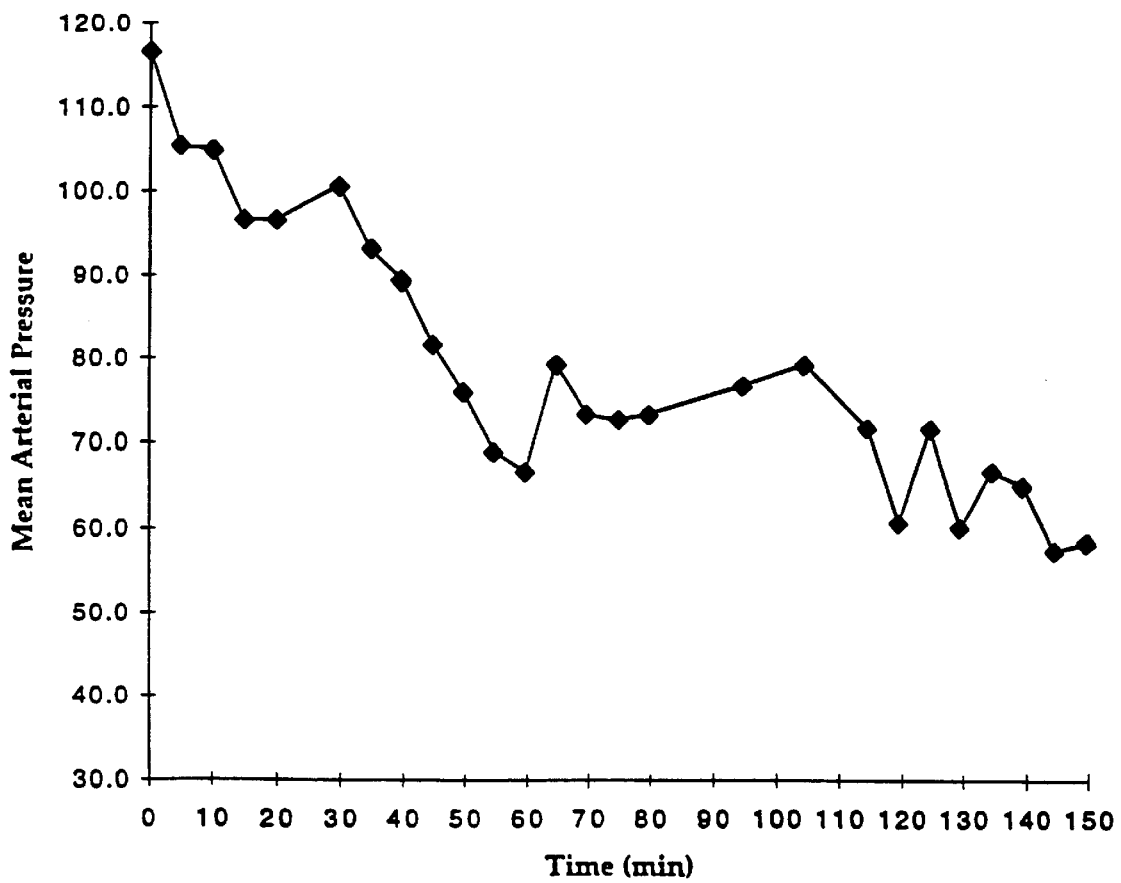
FIG. 4 illustrates the effects of 1.0 nmol VIP in SSL superfused for 30 minutes into the nostril of a hypertensive hamster.

In still another experiment, 1.0 nmol VIP-PEG-liposome composition was superfused for 30 minutes into the nostril of a hypertensive hamster which resulted in a decrease in arterial pressure that persisted at least 150 minutes. These results are shown in FIG. 4. A gradual and sustained decrease in mean arterial pressure to the normal range was detected that lasted throughout the observation period of 2.5 hours.

Figure 5:
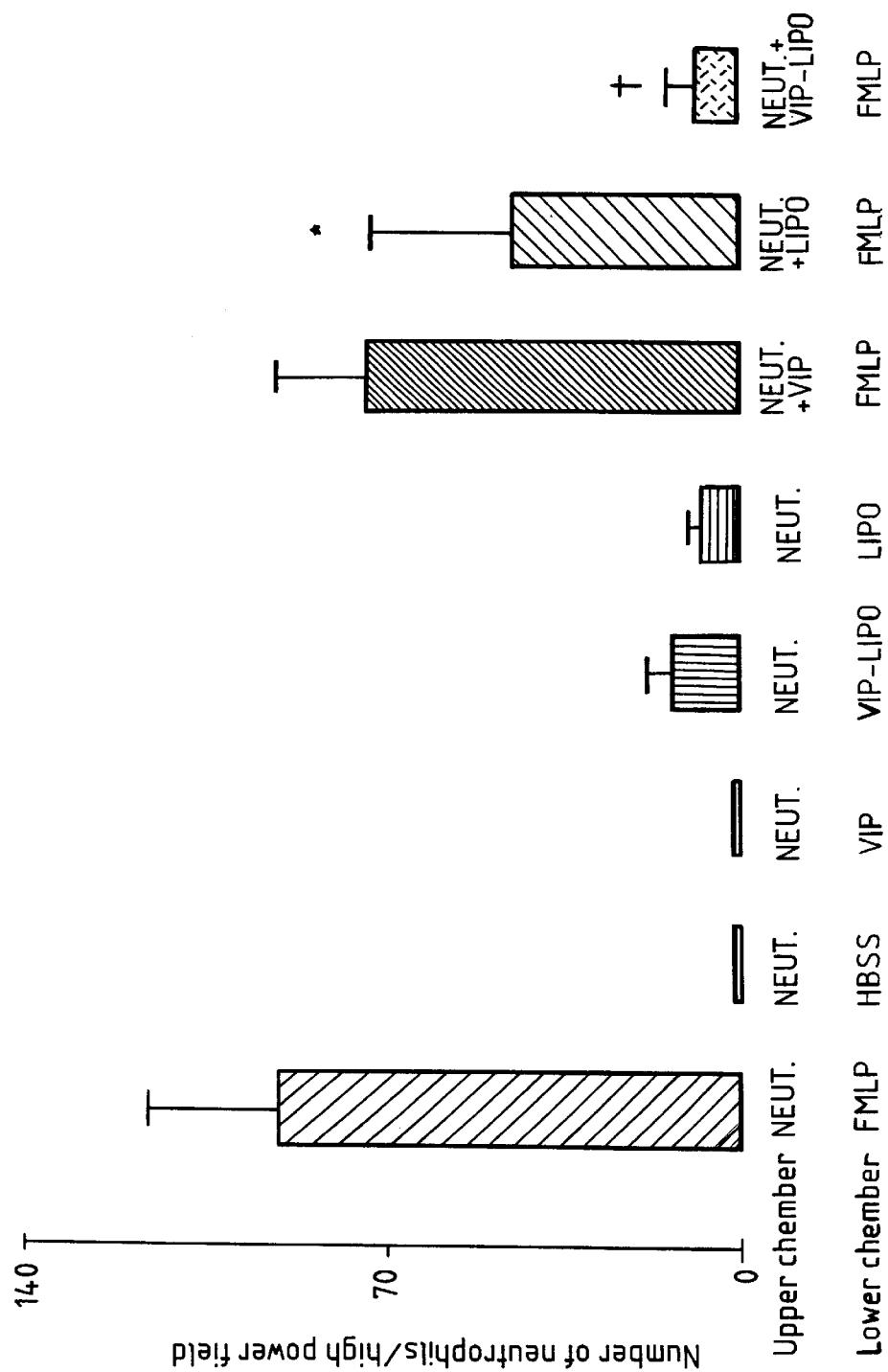
FIG. 5 describes the effect of VIP in SSL, VIP alone, and SLL alone on neutrophil chemotactic response to formyl-methionyl-leucyl-phenylalanine (fmlp) peptide.

Finally, as another experiment the effect of VIP-PEG-liposomes on neutrophil chemotaxis was examined using a two chamber apparatus routinely employed for in vitro analysis of chemotaxis. The results of the experiment are shown in FIG. 5. Neutrophil migration from the upper chamber into the lower chamber in response to formyl-methionyl-leucyl-phenylalanyl (fmlp) peptide in the lower chamber was initially established at a baseline control. Neutrophil migration against media (Hank's balanced salt solution, HBSS) and VIP alone in the lower chamber was shown to be negligible, and minor levels of neutrophil migration were detected against VIP-PEG-liposomes and PEG-liposome in the lower chamber. When neutrophils and VIP were added together in the upper chamber, significant migration was observed against fmlp in the lower chamber, with slightly lower levels of cell migration observed against fmlp with neutrophils and PEG-liposomes together in the upper chamber. Finally, neutrophil migration against fmlp was reduced to almost negligible levels when VIP-PEG-liposomes were added with the cells in the upper chamber. These results indicated that VIP-PEG-liposomes were capable of chemotactic inhibition of neutrophil migration in response to fmlp.

The present invention is further illustrated by way of the following examples. Example 1 is a comparative example describing the state of the art which illustrates that incorporation of a bioactive VIP peptide into liposomes increases the duration and magnitude of the peptide activity when administered to hamsters with spontaneous hypertension. Example 2 relates to an examination of the same biologically active peptide in association with a sterically stabilized liposome (SSL) according to the methods of invention but in which the liposome provides an even more dramatic increase in peptide activity. Example 3 provides an alternative method for preparing an SSL according to the invention wherein differing preparative techniques are shown to result in vastly different levels of peptide activity. Example 4 provides an analysis of morphological features in liposomes prepared by the methods described in Example 3. Example 5 relates to a modified method for producing SSL with a bioactive peptide wherein simplification of the preparative process does not affect peptide activity in vivo. Example 6 describes manufacture and use of diagnostic liposome products for use in acoustic reflective imaging based on echo-reflective properties of the liposomes.

EXAMPLE 1

Bioactivity of Peptides in Conventional Liposomes (Comparative Example)

According to this example, prior art methods for incorporation of VIP into liposomes were reproduced in order to provide a basis for comparison of the methods of the invention. Because previous observations have suggested that VIP plays a role in regulating vasomotor tone, it was first decided to examine VIP activity in situ on peripheral microcirculation as a function of the vehicle used to dissolve and deliver the peptide. More specifically, a first examination was carried out to determine whether topical administration of VIP could elicit vasodilation in peripheral microcirculation of hamsters with spontaneous hypertension and whether encapsulation of VIP into conventional unilamellar liposomes could modulate any observed response.

Adult male hamsters with spontaneous hypertension (n=21) and age- and genetically-matched normotensive controls (n=20) were purchased from the Canadian Hybrid Farns, Halls Harbor, NS, Canada. In preparation, the animals were anesthetized interperitoneally with sodium pentobarbital (6 mg/100 g body weight) and a tracheostomy was performed to facilitate spontaneous breathing. The left femoral vein was cannulated to inject supplemental anesthesia (2 to 4 mg per 100 g body weight per hour) during the experiment. A catheter was inserted into the left femoral artery to record systemic arterial pressure and heart rate. Body temperature was monitored to maintain a constant 37–38° C. throughout the experiment using a heating pad.

In order to visualize microcirculation of the cheek pouch, previously described methods were employed [Gao, et al., *Life Sci.* 64: PL274–PL252 (1994); Mayhan and Joyner, *Microvasc. Res.* 28: 159–179 (1984); Mayban and Rubinstein, *Biochem. Biophys. Res. Commun.* 184:1372–1377 (1992); Raud, *Acta Physiol. Scand. Suppl.* 578:1–58 (1989); Rubinstein and Mayban, *J. Lab. Clin. Med.* 25:313–318 (1995); Rubinstein, et al., *Am. J. Physiol.* 261 (*Heart Circ. Physiol.* 30):111913–111918 (1991); and Suzuki, et al., *Life Sci.* 57:1451–1457 (1995)]. Briefly, the left cheek pouch was spread over a small plastic baseplate, and an incision was made in the outer skin to expose, the cheek pouch membrane. The avascular connective tissue layer was removed, and a plastic chamber was positioned over the baseplate and secured in place by suturing the skin around the upper chamber. This arrangement formed a triple-layered complex: the baseplate, the upper chamber, and the cheek pouch membrane exposed between the two plates. The upper chamber was connected to a reservoir containing warmed bicarbonate buffer (37–38° C.) that allowed continuous suffusion of the cheek pouch. The buffer was bubbled continuously with 95% $N_2$–5% $CO_2$ (pH 7.4). The chamber was also connected via a three-way valve to an infusion pump (Sage Instruments, Cambridge. Mass.) that allowed controlled administration of drugs into the suffusate. This method of animal preparation was similarly utilized in later investigations as indicated below.

Liposomes containing VIP were prepared according to the methods of Gao, et al., *Life Sci.* 64: PL274–PL252 (1994); Gregoriadis and Florence, *Drugs* 45:15–28 (1993); MacDonald, et al., *Biochem. Biophys. Acta* 1061:297–303 (1991); and Suzuki, et al, *Life Sci.* 57:1451–1457 (1995). Briefly, a lipid composition consisting of egg yolk phosphatidylcholine (Sigma, St. Louis, Mo.), egg yolk phosphatidylglycerol (Sigma), and cholesterol (Sigma) at a 4:1:5 molar ratio (total phospholipid content, 5 mg) was mixed in chloroform (Sigma) and the solvent evaporated to dryness. The dried lipid film was resuspended in 100 $\mu$l 0.15 M NaCl solution containing 0.7 mg VIP by vortex mixing and sonication. The suspension was subjected to five cycles of freeze-thawing using a dry ice-ethanol bath and extruded nine times through two polycarbonate filters (pore size 3 $\mu$m; Nuclepore, Pleasanton, Calif.) using a LiposoFast apparatus (capacity of syringe, 0.5 ml; Avestin, Ottawa, ON, Canada). Liposomes were collected using a disposable gel filtration column (Econo-pac 10DG, polyacrylamide gel, 10 ml bed vol.) in 0.15 N NaCl [MacDonald, et al., *Biochim. Biophys. Acta* 1061:297–303 (1991)]; the liposome fraction was recovered in the void volume and stored at 4° C. until use.

Change in arteriolar diameter was determined as follows. Microcirculation in the cheek pouch was epi-illuminated with a fiber-optic light source and observed through a Nikon microscope. The image was projected through the microscope and into a closed-circuit television system that consisted of low-light television camera, television monitor, and videotape recorder (Panasonic. Yokohama. Japan). The inner wall diameter of secondorder arterioles in the cheek pouch was measured from the video display of the microscope image using a videomicrometer (VIA-100, Boeckeler Instruments, Tucson, Ariz.). Calibration of the magnification of the video system was carried out with a microscope stage micrometer to give microvascular dimensions in micrometers. Vessels were chosen for observation on the basis of clarity on the monitor screen and location within the arteriolar branching pattern in the cheek pouch. In each animal, the same arteriolar segment was used to measure changes in inner wall luminal diameter during the experiment. In some studies, animals were used in more than one treatment group once measures of arteriolar diameter from previous interventions returned to baseline.

VIP alone or encapsulated in liposomes was suffused for 7 minutes at a concentration of VIP of either 0.05 or 0.1 nmol peptide, and more than 30 minutes elapsed between subsequent applications of the peptide. Changes in arteriolar diameter before, during, and after topical application of VIP were determined as outlined above. The concentrations of VIP used in these experiments were based on previous studies [Gao, et al, *Life Sci.* 64: PL274–PL252 (1994); Suzuki, et al., *Life Sci.* 57:1451–1457 (1995)].

Results indicated that suffusion of VIP alone at both concentrations was associated with significant vasodilation in normotensive hamsters with the maximal response observed within 4 minutes of the start of suffusion. Arteriolar diameter returned to baseline within 1 minute after suffusion of VIP was stopped. In contrast, suffusion of VIP alone had no significant effects on arteriolar diameter in hamsters with spontaneous hypertension. This blunted response to VIP in hypertensive animals could not be attributed to nonspecific damage to the endothelium because nitroglycerin, an endothelium independent vasodilator in the cheek pouch [Mayban and Rubinstein, *Biochem. Biophys. Res. Commun.* 184:1372–1377 (1992); Rubinstein, et al., *Am. J. Physiol.* 261 (*Heart Circ. Physiol.* 30):111913–111918 (1991)] elicited vasorelaxation of similar magnitude in both groups.

With suffusion of VIP at the same amounts but encapsulated in liposomes, normotensive animals showed significant, concentration-dependent potentiation and prolongation of vasorelaxant effects in comparison with VIP alone. The maximal response was detected 3 to 4 minutes after suffusion began and significant vasodilation persisted almost 9 minutes after suffusion was stopped. In hamsters with spontaneous hypertension, liposome encapsulated VIP produced a significant vasorelaxant effect of magnitude similar to that observed in the nonnotensive animals. A maximal effect was detected within 4 minutes from the start of suffuision and significant vasodilation persisted over 3 minutes after suffusion was stopped. Even though encapsulation of VIP in liposomes was able to restore vasorelaxant effects of the peptide in hamsters with spontaneous hypertension to a magnitude similar to that observed in normotensive animals, the duration of effect was significantly shorter.

These results suggested that vasodilation elicited by VIP in peripheral microcirculation of normotensive hamsters is composed of two components; the first regulating the magnitude of the response and the second its duration. While the former was expressed in both aqueous and lipid environments, the latter was observed only when VIP was partitioned into lipid bilayers [Gao, et al., *Life Sci.* 64: PL274-PL252 (1994); Gregoriadis and Florence, *Drugs* 45:15–28 (1993); MacDonald, et aL, *Biochim. Biophys. Acta* 1061:297–303 (1991); Musso, et al., *Biochemistry* 27: 8174–8181 (1988); Noda, et al., *Biochim. Biophys. Acta* 1191: 324–330 (1994); Robinson, et al., *Biopolymers* 21:1217–1228 (1982); Soloviev, et al., *J. Hyperiens.* 11:623–627 (1993); Suzuki, et al., *Life Sci.* 57:1451–1457 (1995)] which may provide an appropriate environment for π-helix formation in VIP molecules [Noda, et al., *Biochim. Biophys. Acta* 1191: 324–330 (1994); Robinson, et al., *Biopolymers* 21:1217–1228 (1982)]. For reasons that are not entirely clear, the lipid-dependent component of VIP-induced vasodilation in peripheral microcirculation was found to be absent in hamsters with essential hypertension.

EXAMPLE 2

Characterization of Bioactivity in Sterically Stabilized Liposomes

Having demonstrated that VIP encapsulation in conventional liposomes restored capacity of the peptide to induce vasodilation in hamsters with spontaneous hypertension, changes in VIP activity when associated with the sterically stabilized liposomes of the invention were examined.

Normotensive animals were prepared essentially as described in Example 1 with the following changes. Adult male golden Syrian hamsters (n=28;120–140 g body weight) were anesthetized with pentobambital sodium (6 mg/100 g body weight, i.p.) and a femoral vein was cannulated to administer the intravascular tracer, fluorescein isothiocyanate labeled dextran (FITC-dextran dissolved in 1.0 ml saline; molecular mass 70 kDa; 40 mg/100 g body weight and administered over 1 minute) and supplemental anesthesia (2–4 mg/100 g body weight/hour). To visualize changes on microcirculation of the cheek pouch, the procedure described above in Example 1 was employed.

Sterically stabilized liposomes (SSL) were prepared as follows. Egg yolk phosphatidylcholine (Sigma), egg yolk phosphatidylglycerol (Sigma), cholesterol (Sigma) and polyethylene glycol (molecular mass, 1,900) linked to distearoyl-phosphatidylethanolamine (molar ratio, 5:1:3.5:0.5; phospholipid content, 17 mmol) were dissolved and mixed in chloroform [Gao, et al., *Life Sci.* 54: PL247–PL252 (1994); Lasic and Martin. *Stealth Liposomes*, CRC Press, Inc.:Boca Raton, Fla., 1995; Suzuki, et al., *Am. J. Physiol.* 271:H282–H287 (1996)]. The solvent was evaporated at 45° C. in a rotary evaporator under vacuum overnight. The resulting lipid film was rehydrated in 250 ml saline, vortexed, bath-sonicated for 5 minutes, and extruded through stacked polycarbonate filters using the LiposoFast apparatus (consecutive pore sizes: 200, 100, 50 nm; AVEsnN. Inc., Ottawa, ON, Canada). Human VIP (0.4 mg) and trehalose (30 mg), a cryoprotectant, were added to the extruded suspension, which was then frozen in acetone-dry ice bath and lyophilized overnight at −46° C. under constant pressure (Foreseen 6, Labconco, Kansas City, Mo.). Thereafter, the lyophilized "cake" was resuspended in 250 ml deionized water. VIP associated with SSL was separated from free VIP by column chromatography (Bio-Gel A-5 m, Bio-Rad Laboratories, Richmond, Calif.) and stored at 4° C. for a maximum of 15 days. The size of SSL was 250±50 nm as determined by quasi elastic light scattering (Nicomp model 270 submicron particle sizer, Pacific Scientific, Menlo Park, Calif.). The phospholipid concentration in SSL was determined by the Barlett inorganic phosphate assay [Kates, M. *Techniques in Lipidology*, Work and Work (Eds.) Elsevier:New York, New York (1972) pp. 354–356]. VIP concentration in SSL was determined by a commercially-available ELISA assay kit (Peninsula Laboratories, Belmont, Calif.) after dissolving SSL with sodium dodecyl sulfate 1%. The recovery was 30% for VIP and 50% for phospholipids, giving a ratio of 0.004 mole VIP/mole of phospholipids.

Determination of arteriolar diameter was carried out as described above in Example 1. In a first group of animals, 0.42 and 0.85 nmol VIP in SSL were suffused for 1 hour in an arbitrary order. At least 45 minutes elapsed between subsequent suffusions of VIP in SSL [Suzuki, et al., *Life Sci.* 57:1451–1457 (1995); Suzuki, et al., *Am. J. Physiol.* 271:H282–H287 (1996)]. Arteriolar diameter was measured immediately before suffusion, every minute during suffusion of VIP in SSL and at 5 minute intervals thereafter. Previous observations indicated that suffusion of saline alone for the entire duration of the experiment was associated with no significant change in arteriolar diameter. In another group of animals, VIP in SSL (0.1 nmol) or empty SSL at a concentration equivalent to that in 0.1 nmol VIP in SSL (18 nmol/ml phospholipids) were suffused for 7 minutes.

Suffusion of animals in the first group with 0.42 nmol and 0.85 nmol VIP in SSL for 1 hour produced a significant, concentration dependent, and prolonged increase in arteriolar diameter. Significant vasodilation was observed within 2 minutes of the start of suffusion which maximal within 5 minutes of the beginning of suffusion. Arteriolar diameter returned to baseline levels 50 minutes after suffusion of VIP in SSL was stopped. Suffusion with empty SSL for 1 hour had no significant effect on arteriolar diameter.

Suffusion of normotensive animals in the second group with 0.1 nmol VIP in SSL also elicited a significant increase in arteriolar diameter from baseline but to a lessor extent than that observed in first group. Arteriolar diameter returned to baseline 13 minutes after suffusion of VIP in SSL was stopped. Suffusion of empty SSL had no significant effects on arteriolar diameter. Even though vasodilation for 1 hour was greater than that observed for 7 minute suffusion, the results indicated that using 0.1 nmol peptide would still produce a significant change over baseline.

In order to determine whether the vasodialating effects of VIP in SSL were caused in part by non-specific damage to microvessels resulting in macromolecular efflux from the cheek pouch [Gao, et al., *Life Sci.* 54: PL247–PL252 (1994); Raud, *Acta Physiol. Scand. Suppl.* 578:1–58 (1989)], two indices were used to determine clearance of macromolecules from the cheek pouch under control and experimental conditions as previously described [Gao, et al., *Life Sci.* 54: PL247–P1252 (1994); Raud, *Acta Physiol. Scand. Suppl.* 578:1–58 (1989)]. The first was a determination of the number of fluorescent "spots" or leaky sites around post-capillary venules and the second was a determination of FITC-dextran clearance from the cheek pouch.

After suffusing animals with bicarbonate buffer for a 30 minute equilibration period, FITC-dextran was administered intravenously. VIP in SSL (0.1 nmol) was then suffused for 7 minutes and the number of leaky sites was determined initially every minute for 7 minutes, and then at 5 minute intervals for 60 minutes thereafter. Clearance of FITC-dextran was determined before suffusion of VIP in SSL and every 5 minutes during and after suffusion for 60 minutes [Gao. et al., *Life Sci.* 54: PL247-PL252 (1994)].

Results indicated that suffusion of nmol VIP in SSL was not associated with visible leaky site formation. Likewise, clearance of FITC-dextran during suffusion of saline was essentially identical to clearance during suffusion of VIP in SSL.

Combined these results indicated that suffusion of VIP in SSL onto hamster cheek pouch elicits significant and prolonged concentration-dependent vasodilation. This response was not related to non-specific damage to microvascular endothelium because arteriolar diameter returned to baseline once suffusion of VIP in SSL was stopped and because VIP in SSL did not elicit macromolecular efflux from post-capillary venules in the cheek pouch. These results suggested that VIP in SSL could be useful in restoring vascular reactivity in the peripheral microcirculation in certain diseases where endothelium-dependent vasodilation is impaired, such as hypertension, congestive heart failure, diabetes mellitus and impotence [Paul and Ebadi, *Neurochem. Int.* 23:197–214 (1993); Suzuki, et al., *Am. J. Physiol.* 271:H282–H287 (1996)].

EXAMPLE 3

Comparison of Bioactivity as a Function of Liposome Preparation

Having demonstrated that VIP in SSL exhibits enhanced bioactivity over VIP preparations in conventional liposomes, alternative methods of preparation were examined in order to determine optimal compositions, methods of their preparation, and to further characterize the bioactivity of VIP in SSL.

Two different methods of liposome preparation methods were utilized. In both, the lipids distearoyl-phophatidylethanolamine (PEG-DSPE) (Sequus Pharmaceuticals, Menlo Park. Calif.), Egg yolk phosphatidylcholine (PC) (Sigma Chemical Co., St. Louis, Mo.), and egg yolk phosphatidylglycerol (PG) (Sigma Chemical Co., St. Louis, Mo.), were combined with cholesterol (Sigma Chemical Co., St. Louis, Mo.) at a PEG-DSPE:PC:PG:Chol molar ratio of 0.5:5:1:3.5. Total phospholipid content of the mixture was 17 pmol. The mixture was mixed in chloroform in a round bottom flask, the solvent evaporated at 45 ° C. in a rotary evaporator (Labconco, Kansas City, Mo.) and the mixture desiccated under vacuum overnight.

In a first method of preparation (not contemplated by the invention), VIP was initially mixed with a lipid composition followed by extrusion and repeated freezing and thawing to produce liposomes. Briefly, the dry lipid film was rehydrated with 250 $\mu$l 0.15 M saline (0.9% w/w NaCl) containing 0.4 mg VIP (American Peptide Co., Sunnyvale, Calif.). The mixture was vortexed, sonicated for 5 minutes in a 175.5W water bath sonicator (Fisher Scientific, Itasca, Ill.), and freeze-thawed five times in an acetone-dry ice bath. The suspension was extruded through polycarbonate filters using the Liposofast apparatus (pore size 200 nm, AVESTIN, Inc., Ottawa, ON, Canada). The liposome-associated VIP was separated from the free VIP by column chromatography (BioGel A-5 m, Bio-Rad Laboratories, Richmond, Calif.) and stored at 4° C. until use. Column elution was carried out using the 15 M saline solution described above. Vesicle size was determined by quasi elastic light scattering [Alkan-Onyuksel, et aL, *J. Pharm. Sci.* In. press (1996)] with a Nicomp 270 particle sizer (Particle Sizing Systems, Santa Barbara, Calif.) and liposomes prepared by this method were found to have an average mean diameter of 224±36 nm.

In a second method of preparation which is contemplated by the invention, a lipid mixture was first extruded, after which VIP was mixed with the formed liposomes. Briefly, a dry lipid film prepared as before was rehydrated with 250 ml 0. 15 M saline without VIP. The mixture was vortexed, bath-sonicated for 5 minutes, and extruded through stacked polycarbonate filters of 200, 100, and 50 nm pore size to give a vesicle size of about 80 nm. VIP (0.4 mg) and trehalose (30 mg) (Sigma Chemical Co., St. Louis, Mo.) as a cryoprotectant were added in powder form to the extruded suspension. The mixture was incubated either at room temperature for two hours or overnight at 4° C., frozen in an acetone-dry ice bath, and lyophilized at −46° C. under a pressure of approximately 5 ×10$^{-3}$ MBar overnight (Labconco "Freezone 6", Kansas City, Mo.). The lyophilized "cake" was resuspended with 250 $\mu$l deionized water. During freeze-drying, VIP and phospholipid bilayers were in close contact which provides a promotes passive drug loading. Column separation and storage conditions were the same as above. Liposomes prepared by this method were found to have an average diameter of 250±50 nm by the method described above, suggesting that freeze-drying permitted vesicle fusion. VIP concentration in the liposomes was determined after treatment with sodium dodecyl sulfate 1% by a VIP ELISA assay kit (Peninsula Laboratories, Belmont, Calif.) and the phospholipid concentration was evaluated by the Barlett inorganic phosphate assay [M. Kates. *Techniques in Lipidology*, Work and Work (Eds), Elsevier, New York (1972) pp. 354–356]. For both methods of preparation, approximately 30% of the starting VIP was found to be liposome associated and approximately 50% of the starting phospholipids was recovered giving a ratio of approximately 0.004 mole VIP/mole of phospholipid.

Two types of in vivo experiments were performed to determine the vasorelaxant and hypotensive effects of VIP in liposomes prepared by the two methods. In a first series of experiments, the bioactivity of VIP in the liposome preparations was examined as a function of vasodilation, while in the second series of experiments, the duration and efficacy of VIP in the two liposome preparations on mean arterial pressure was measured.

In the first experiments, the bioactivity of VIP in the liposome preparations was measured as a function of change in arteriolar diameter in hamster cheek pouch. Adult male golden Syrian hamsters (n =9) (Sasco, Omaha, Nebr.) were prepared as previously described [Suzuki, et aL, $Life$ $Sci.$ 57(15):1451–1457 (1995); Suzuki, et al., $Am.$ $J.$ $Physiol.$ 271:11282–H287 (1996); Suzuki, et al., $Am.$ $J.$ $Physiol.$ In press (1996)] and anesthetized with pentobarbital sodium (2–4 mg/100 g body weight) via a cannulated femoral vein. A femoral artery was cannulated to record systemic arterial pressure and heart rate using a transducer and a strip-chart recorder (Model 260, Gould Instrument Systems Inc., Valley View, Ohio). The visualization of the microcirculation of the cheek pouch, an established animal model to investigate the vasoactive effects of neuropeptides in situ, was conducted as previously described [Suzuki, et al., $Life$ $Sci.$ 57(15) :1451–1457 (1995); Suzuki, et al., $Am.$ $J.$ $Physiol.$ 271:11282-H287 (1996); Suzuki, et al., $Am.$ $J.$ $Physiol.$ In press (1996)]. The inner-wall diameter of second order arterioles in the hamster cheek pouch was measured from the video display of the microscope image using a videomicrometer (VIA 100; Boeckeler Instruments. Tucson, Ariz.). In each animal, the same arteriolar segment was used to measure changes in diameter during the experiment. The hamster cheek pouch was first suffused with bicarbonate buffer during a 30 minutes equilibration period, and then with 1.4 ml of each liposome preparations described above for 7 minute.

VIP in liposomes prepared by the first method, outside the scope of the invention, did not elicit an increase in arteriolar diameter significantly different from previously reported observations with 0.1 nmol VIP dissolved in saline, i.e. approximately 10% [Suzuki, et al., $Life$ $Sci.$ 57(15): 1451–1457 (1995)]. When this observation is compared to the previous observation that VIP in conventional liposomes prepared with the same method but without an extrusion step shown enhanced and prolonged effects in situ [Suzuki, et al., $Life$ $Sci.$ 57(15):1451–1457 (1995)], three possibilities are suggested to account for the loss of activity of VIP in SSL prepared by the present method; the extrusion process, the lipid composition or the smaller size of the vesicles. Regardless of the reason than SSL prepared by this method did elicit an enhanced or prolonged effect on arteriolar diameter, this result is significant in demonstrating that SSL in general are not amenable to the present invention.

VIP (0.1 nmol) in liposomes prepared by the second method and within the scope of the invention, elicited a significant increase in arteriolar diameter from baseline values and the increase persisted for 9 to 16 minutes after suffusion was stopped. This result was more similar to previous observations using conventional liposomes [Suzuki, et al., $Life$ $Sci.$ 57(15):1451–1457 (1995)].

In examining the duration and efficacy of VIP in the two liposome preparations on mean arterial pressure, the following procedure was carried out. Adult mate hamsters with spontaneous hypertension (n=12) were obtained from the Canadian Hybrid Farms (Hall Harbour, Nova Scotia, Canada). Approximately 500 $\mu$l each of three test preparations, liposomes prepared by the second method above, VIP in aqueous solution, and liposomes without VIP, were injected administered over the course of 1 minute in the femoral vein. Continuous anesthesia of the animals limited the duration of the experiment to 6 hours.

Figure 6:
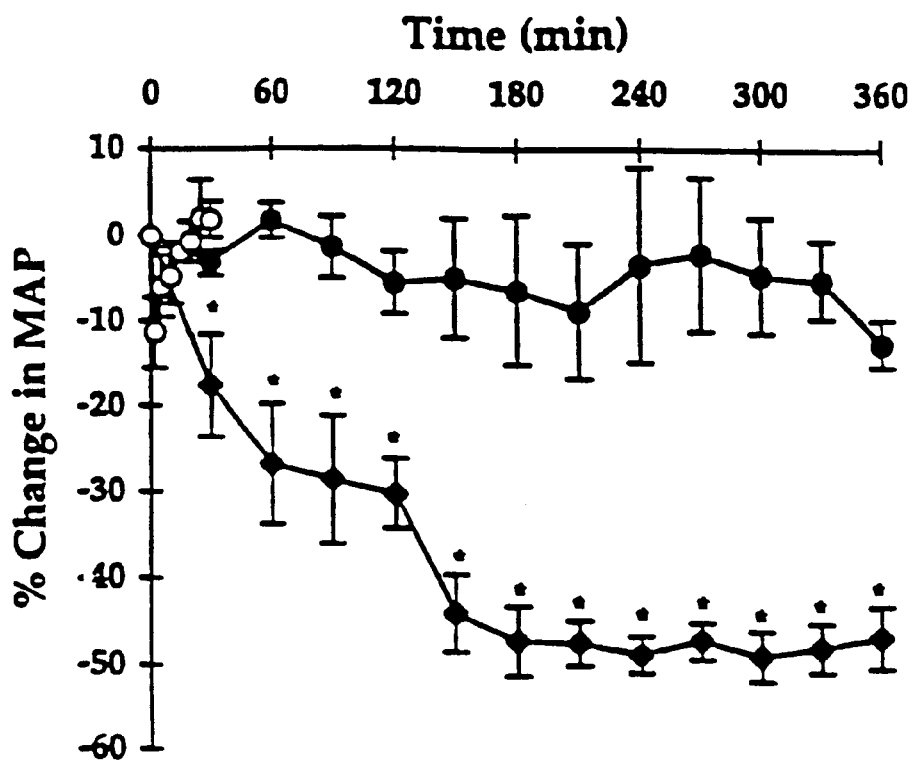
FIG. 6 depicts the drop in mean arterial blood pressure using liposomes prepared by the methods described in Example 3; an asterisk in the figure indicates a statistically significant difference between VIP in SSL and SSL lacking VIP.

After injection of 0.1 nmol liposome-associated VIP, a significant and gradual decrease in mean arterial pressure up to 50% was observed in the first 2.5 hours which persisted for the 6 hour observation period of the experiment as shown in FIG. 6. No significant effect on mean arterial pressure was observed using empty liposomes or VIP in aqueous solution. These data suggest that intravenously administered VIP in SSL successfully normalized the mean arterial pressure of hamsters with spontaneous hypertension for at least 6 hours. Interestingly, the dose required to produce normal blood pressure was very low compared to previous observations wherein the same amount of VIP in conventional liposomes produced a 30% decrease in mean arterial pressure of normotensive hamsters [Gao, et al., $Life$ $Sci.$ 54:PL247PL252 (1994)], but this observation may be attributed to a higher sensitivity of hamsters with spontaneous hypertension to VIP.

Since SSL having the same composition and size prepared by the method of the invention (i.e., the second method) retained the VIP activity, the results suggest that extrusion was responsible for the loss of bioactivity in the first liposome preparation. This possibility is consistent with a previous demonstration wherein interleukin-2 was shown to lose more than 25% activity after extrusion [Kedar, et al., $J$ $Immunother.$ 16:47–59 (1994)], but inconsistent with an observation that vasopressin was not significantly affected by extrusion [Woodle, et al., $Pharm$ $Res.$ 9(2):260–265 (1992)].

EXAMPLE 4

Morphological Evaluation of SSL

For morphological evaluation of vesicle prepared by both methods described in Example 3, liposomes were prepared for freeze-fracture according to standard techniques as reported previously [Alkan-Onyuksel, et al., $J.$ $Pharm.$ $Sci.$ In press (1996)]. Briefly, drops of each liposome suspension were frozen in liquid-nitrogen cooled Freon 22, fractured using a Balzers BAF 301 freeze-etch unit at −115° C., and coated with platinum and carbon. The replicas were cleansed in a minimum of two changes of sodium hypochlorite, washed with distilled water, dried, collected on 200 mesh copper grids, examined and photographed with a JEOL 100CX transmission electron microscope at 80 kv.

Examination of SSL prepared by the method of the invention revealed multivesicular vesicles, suggesting that freeze-drying caused some fusion of the small pre-extruded SSL to form vesicle in a vesicle structures, consistent with the observed increase in mean diameter from 80 nm to 250 mn. This observation is consistent with previously reported fusion events during the freeze-drying/reconstitution process of SSL. [Szucs and Tilcock, $Nucl.$ $Med.$ $Biol.$ 22:263–268 (1995)]. Possibly, the formation of larger vesicles may have promoted the entrapment of VIP molecules inside the final liposomes, while retaining a rather small mean size and distribution required for long circulation times.

EXAMPLE 5

Peptide Activity in a Simplified Liposome Preparation

According to this example a simple method for producing SSL associated with a biologically active peptide is provided which acts to maintain the resulting liposomes at a size approximately less than 200 nm. In addition an alternative method of preparation was examined and the effects of the preparative method on peptide activity determined.

Egg yolk PC, egg yolk PG, cholesterol, and PEG-DSPE were mixed in chloroform at a molar ratio of 5:1:3.5:0.5 and the solvent evaporated using a water bath at 45° C. The lipid film was dried overnight and resuspended in 250 $\mu$l saline. The mixture was vortexed, sonicated for 5 minutes and extruded through stacked polycarbonate filters using a LiposoFast apparatus. Human VIP was added to the resulting liposomes having an average diameter of less than 300 nm and the mixture incubated overnight at 4° C. Free VIP was separated from the VIP-associated liposomes using a Biogel A-5 m column and collected liposomes stored under argon at 4° C. until use. Size of the liposomes determined by quasi electric light scattering indicated an average diameter of 162±59 nm. Phospholipid concentration and VIP recovery were determined as described above and found to be 44% for VIP and 50% for phospholipid, giving a VIP:phospholipid molar ratio of 0.006.

Adult male golden Syrian hypertensive hamsters were prepared for intravital microscopy, cheek pouch microcirculation observed and measured, and mean arterial pressure determined, each technique as described above. Measurements were made with administration of VIP in aqueous solution, VIP in SSL as prepared above, and SSL in the absence of VIP.

Suffusion of VIP in SSL for 7 minutes was associated with a significant, concentration dependent and prolonged increase in arteriolar diameter. Significant vasodilation was observed within 1 minute from the start of suffusion and was maximal within the first 5 minutes. Arteriolar diameter returned to normal levels within 8 minutes after suffusion was stopped. VIP in aqueous solution and empty SSL has no effects.

VIP in SSL also elicited a significant reduction in mean arterial pressure with the maximal effect observed within 30 minutes from the onset of suffusion. Blood pressure remained low during the entire course of the 6 hour observation period. As before, VIP in aqueous solution and empty SSL had no effect.

These results indicated that the dehydration/rehydration step described in Example 3 is not necessary to formation of active liposome preparations. More importantly, liposomes prepared by this method retained an average diameter of less than 200 nm and retained equal, if not higher, VIP activity than either liposome preparation described in Example 3. As an additional advantage, the VIP:phospholipid ratio which resulted from this preparative method was higher (0.006 vs. 0.004) when compared to the method of Example 3.

EXAMPLE 6

SSL in Acoustic Reflectivity Assays

SSL including VIP were prepared and utilized for imaging using acoustic reflectivity measurements as follows.

Liposomes prepared as described in Example 3 were transferred to liquid scintillation vials and imaged with a 20 MHz high-frequency intravascular ultrasound (IVUS) imaging catheter (Boston Scientific Inc., Sunnyvale, Calif.). The IVUS catheter was passed through the vial cap and secured. Instrument settings for gain. zoom, compression, and rejection levels were optimized at the initiation of the experiment and held constant for all samples. Images were recorded onto ½ inch VHS videotape in real time for subsequent playback and image analysis.

Relative echogenicity (apparent brightness) of liposome formulations was objectively assessed by computer-assisted videodensitometry. The process involved acquisition, preprocessing, automated liposome identification, and gray scale quantification. Image processing and analysis were performed with Image Pro Plus Software (Ver. 1.0, Media Cybernetics, Silver Springs, Md.) running on a dedicated computer (486 CPU, 66 MHz). Randomly selected IVUS images were acquired from video tape for each liposome formulation. Images were digitized to 640×480 pixels spatial resolution (approximately 0.045 mm/pixel) and 8 bit (256 levels) amplitude resolution. all analyzed IVUS data were collected at a fixed instrument gain level. The distribution of gray scale values within the image was then adjusted to cover the entire range of possible gray levels using a linear transformation algorithm (i.e., dynamic range was maximized). Image brightness was subjectively scaled such that a reference feature, common to each image, retained a constant gray scale value over all images. An automated-liposome detection routine was then run to identify liposomes suspended in solution within an annular region of interest set at a constant radial distance from the imaging catheter. The automated liposome detection routine identified all "bright" objects within the analysis annulus having a gray scale level greater than 29, a roundness ratio (i.e., ratio of maximum diameter:minimum diameter) less than 2.5, and a size greater than 4 pixels. This procedure excluded virtually all imaging artifacts from the detection algorithm. Thus, object identified were considered to be "liposomes." Each liposome was outlined and numbered by the computer program. The average gray scale and size of each value of all pixels identified as "liposomes" with a given image was then computed and used to characterize the echogenicity of a given liposome formulation. The results of these experiments demonstrate that the acoustic reflectance of the VIP liposome preparation has a gray scale of 119 (on a gray scale of 0 to 255 with 255 as pure white and 0 as pure black). Larger liposomes produced using lyophilization methods described in PCT Publication WO 93/20802 are characterized by an acoustic reflectance of about 110–120 while liposomes comprising contrast media such as Albunex® have an acoustic reflectance of about 110–120. Accordingly, the invention provides small diameter liposomes while retaining their acoustic imaging properties.

Numerous modifications and variations in the invention as set forth in the above illustrative examples are expected to occur to those skilled in the art. Consequently only such limitations as appear in the appended claims should be placed on the invention.

What is claimed is:

1. A method of preparing a biologically active liposome product comprising a biologically active amphipathic compound in association with a liposome; said method comprising the steps of:

a) mixing a combination of lipids wherein said combination includes at least one lipid component covalently bonded to a water-soluble polymer;

b) forming sterically stabilized liposomes from said combination of lipids;

c) obtaining liposomes having an average diameter of less than about 300 nm; and d) incubating liposomes from step (c) with a biologically active amphipathic compound under conditions in which said compound becomes associated with said liposomes from step (c) in an active conformation.

2. The method according to claim 1 wherein said biologically active liposome products comprise unilamellar liposomes.

3. The method according to claim 1 comprising the step of forming multivesicular liposomes.

4. The method according to claim 3 wherein said multivesicular liposomes are produced by carrying out the steps of sequentially dehydrating and rehydrating liposomes obtained in step (c) with said biologically active peptide.

5. The method according to any one of claims 1 through 4 wherein said water soluble polymer is polyethylene glycol (PEG).

6. The method according to claim 1 wherein the amphipathic compound is characterized by having one or more α- or π-helical domains in its biologically active conformation.

7. The method according to claim 6 wherein the compound is a member of the vasoactive intestinal peptide (VIP)/growth hormone releasing factor (GRF) family of peptides.

8. The method according to claim 7 wherein the peptide is VIP.

9. The method according to claim 1 wherein the liposomes obtained in step (c) have an average diameter or less than about 200 nm.

10. The method according to claim 9 wherein the liposomes obtained in step (c) have an average diameter or less than about 100 nm.

11. The method according to any one of claims 1, 8, or 9 wherein the liposomes are obtained in step (c) by extrusion to form liposomes having a selected average diameter.

12. The method according to any one of claims 1, 8, or 9 wherein the liposomes are obtained in step (c) by size selection.

13. The method of claim 1 wherein the combination of lipids consists of distearoyl-phosphatidylethanolamine covalently bonded to PEG (PEG-DSPE), phosphatidylcholine (PC), and phosphatidylglycerol (PG) in further combination cholesterol (Chol).

14. The method of claim 13 wherein the combination of lipids are combined with cholesterol in a PEG-DSPE:PC:PG:Chol molar ratio of 0.5:5:1:3.5.

* * * * *